US012797017B2

(12) United States Patent
Mason et al.

(10) Patent No.: US 12,797,017 B2
(45) Date of Patent: Nov. 17, 2026

(54) TECHNIQUES FOR PROCESSING CBCT PROJECTIONS

(71) Applicant: Elekta LTD., Montreal (CA)

(72) Inventors: Jonathan Hugh Mason, Edinburgh (GB); Joseph Stancanello, Gif sur Yvette (FR); Martin Emile Lachaine, Montreal (CA); Roushanak Rahmat, Crawley (GB)

(73) Assignee: Elekta LTD., Montreal (CA)

( * ) Notice: Subject to any disclaimer, the term of this patent is extended or adjusted under 35 U.S.C. 154(b) by 618 days.

(21) Appl. No.: 18/157,524

(22) Filed: Jan. 20, 2023

(65) Prior Publication Data

US 2024/0245363 A1 Jul. 25, 2024

(51) Int. Cl.
*A61B 6/03* (2006.01)
*A61B 6/40* (2024.01)
(Continued)

(52) U.S. Cl.
CPC .............. *A61B 6/03* (2013.01); *A61B 6/4085* (2013.01); *G06T 11/005* (2013.01)

(58) Field of Classification Search
CPC ......... A61B 6/4085; A61B 6/03; A61B 6/032; A61B 6/5205; A61B 6/5258;
(Continued)

(56) References Cited

U.S. PATENT DOCUMENTS 10,335,611 B2 7/2019 Maurer, Jr. et al.
10,573,032 B2 * 2/2020 Xu ............................ G06T 5/77
(Continued)

FOREIGN PATENT DOCUMENTS

CN 108389242 8/2018
CN 109064521 12/2018
(Continued)

OTHER PUBLICATIONS

"International Application Serial No. PCT CA2024 050048, International Search Report mailed Mar. 27, 2024", 6 pgs.
(Continued)

*Primary Examiner* — Casey Bryant
(74) *Attorney, Agent, or Firm* — Schwegman Lundberg & Woessner, P.A.

(57) ABSTRACT

Systems and methods are disclosed for image processing of cone beam computed tomography (CBCT) image data, in connection with radiotherapy planning and treatments. Example operations for training of a predictive regression model include: obtaining a reference medical image of an anatomical area (e.g., from a reference CT image); generating variation images that provide variation in representations of the anatomical area (e.g., from deformation or geometric transformation); identifying projection viewpoints (e.g., from projection capture angles in a CBCT projection space) for each of the plurality of variation images; generating, at each of the projection viewpoints, a set of CBCT projections and a corresponding set of simulated aspects of the CBCT projections; training an algorithm in the regression model, using the corresponding sets of the CBCT projections and the simulated aspects of the CBCT projections. Corresponding operations for the use of the regression model, including in radiotherapy treatments, are also disclosed.

23 Claims, 17 Drawing Sheets

(51) Int. Cl.
*G06T 12/10* (2026.01)
*G06T 11/00* (2006.01)

(58) Field of Classification Search
CPC ......... G01T 2211/441; G01T 2211/452; G01T 11/005; A61N 2005/1041; A61N 2005/1061
See application file for complete search history.

(56) References Cited

U.S. PATENT DOCUMENTS

| | | | | |
|---|---|---|---|---|
| 11,501,438 | B2 * | 11/2022 | Xu | G06T 12/30 |
| 12,217,335 | B2 | 2/2025 | Lee et al. | |
| 12,329,986 | B2 | 6/2025 | Mason et al. | |
| 2013/0051519 | A1 | 2/2013 | Yang et al. | |
| 2018/0144510 | A1 | 5/2018 | Lachaine | |
| 2018/0330233 | A1 | 11/2018 | Rui et al. | |
| 2018/0374245 | A1 | 12/2018 | Xu et al. | |
| 2019/0070436 | A1 | 3/2019 | Willcut et al. | |
| 2019/0102916 | A1 | 4/2019 | Palma et al. | |
| 2019/0333219 | A1 | 10/2019 | Xu et al. | |
| 2020/0129780 | A1 | 4/2020 | Lachaine et al. | |
| 2020/0129784 | A1 | 4/2020 | Beriault et al. | |
| 2020/0151922 | A1 | 5/2020 | Xu et al. | |
| 2020/0279410 | A1 * | 9/2020 | Lee | A61B 6/032 |
| 2020/0279411 | A1 | 9/2020 | Atria et al. | |
| 2021/0264591 | A1 | 8/2021 | Park et al. | |
| 2021/0290194 | A1 | 9/2021 | Bai et al. | |
| 2021/0304402 | A1 | 9/2021 | Morgas et al. | |
| 2022/0058437 | A1 * | 2/2022 | Soni | G06N 3/08 |
| 2022/0415021 | A1 | 12/2022 | Ewald et al. | |
| 2023/0274473 | A1 | 8/2023 | Hua et al. | |
| 2024/0202943 | A1 | 6/2024 | Schmidt-richberg et al. | |
| 2024/0245932 | A1 | 7/2024 | Mason et al. | |
| 2024/0249451 | A1 | 7/2024 | Mason et al. | |

FOREIGN PATENT DOCUMENTS

| | | | |
|---|---|---|---|
| CN | 110310346 | 10/2019 | |
| CN | 114004912 | 2/2022 | |
| CN | 121219784 | 12/2025 | |
| CN | 121285836 | 1/2026 | |
| CN | 121358523 | 1/2026 | |
| EP | 4235581 | 8/2023 | |
| WO | 2019063760 | 4/2019 | |
| WO | 2019195695 | 10/2019 | |
| WO | 2022036442 | 2/2022 | |
| WO | 2022096312 | 5/2022 | |
| WO | 2022243391 | 11/2022 | |
| WO | 2024152109 | 7/2024 | |
| WO | 2024152114 | 7/2024 | |
| WO | 2024152123 | 7/2024 | |
| WO | WO-2024152109 A1 * | 7/2024 | A61B 6/5282 |
| WO | WO-2024152114 A1 * | 7/2024 | A61B 6/03 |

OTHER PUBLICATIONS

"International Application Serial No. PCT CA2024 050048, Written Opinion mailed Mar. 27, 2024", 5 pgs.
"International Application Serial No. PCT CA2024 050042, International Search Report mailed Apr. 5, 2024", 6 pgs.
"International Application Serial No. PCT CA2024 050042, Written Opinion mailed Apr. 5, 2024", 10 pgs.
"International Application Serial No. PCT CA2024 050059, International Search Report mailed May 6, 2024", 5 pgs.
"International Application Serial No. PCT CA2024 050059, Written Opinion mailed May 6, 2024", 8 pgs.
Adler, Jonas, "Learned Primal-dual Reconstruction", IEEE Transactions on Medical Imaging vol. 37, Issue 6, (Jul. 5, 20118), 11 pgs.
Maier, Joscha, "Deep Scatter Estimation (DSE): Accurate Real-Time Scatter Estimation for X-Ray CT Using a Deep Convolutional Neural Network", Journal of Nondestructive Evaluation, (Jul. 2018), 9 pgs.
Maier, Joscha, "Real-time scatter estimation for medical CT using the deep scatter estimation: Method and robustness analysis with respect to different anatomies, dose levels, tube voltages, and data truncation", Med. Phys. 46 (1), (Jan. 2019), 13 pgs.
Mason, Jonathan H., "Quantitative cone-beam CT reconstruction with polyenergetic scatter model fusion", Physics in Medicine and Biology 63.22, (Jan. 2020), 28 pgs.
Mason, Jonathan H., "Polyquant CT: direct electron and mass density reconstruction from a single polyenergetic source", Physics in Medicine and Biology 62.22, (2019), 23 pgs.
Mason, Jonathan Hugh, "Quantitative Cone-Beam Computed Tomography Reconstruction for Radiotherapy Planning", The University of Edinburgh., (Oct. 2018), 194 pgs.
Nomura, Yusuke, "Projection-domain scatter correction for cone beam computed tomography using a residual convolutional neural network", Med Phys. 46(7), (Jul. 2019), 33 pgs.
Walczak, Michal, "Experimental evaluation of polychromatic reconstruction for quantitative CBCT", Seventh International Conference on Image Formation in X-RayComputed Tomography (ICIFXCT 2022), (Oct. 2022), 6 pgs.
Xie, Shipeng, "Scatter Artifacts Removal Using Learning-Based Method for CBCT in IGRT System", IEEE Access, (Dec. 2018), 7 pgs.
"U.S. Appl. No. 18/157,531, Notice of Allowance mailed Feb. 21, 2025", 8 pgs.
"U.S. Appl. No. 18/157,531, Corrected Notice of Allowability mailed Mar. 4, 2025", 2 pgs.
"U.S. Appl. No. 18/157,504, Restriction Requirement mailed Apr. 14, 2025", 6 pgs.
"U.S. Appl. No. 18/157,504, Response filed Jun. 13, 2025 to Restriction Requirement mailed Apr. 14, 2025", 9 pgs.
"U.S. Appl. No. 18/157,504, Non Final Office Action mailed Aug. 11, 2025", 16 pgs.
"International Application Serial No. PCT CA2024 050048, International Preliminary Report on Patentability mailed Jul. 31, 2025", 7 pgs.
"International Application Serial No. PCT CA2024 050042, International Preliminary Report on Patentability mailed Jul. 31, 2025", 12 pgs.
"U.S. Appl. No. 18/157,504, Final Office Action mailed Dec. 11, 2025", 20 pgs.
"U.S. Appl. No. 18/157,504, Examiner Interview Summary mailed Feb. 6, 2026", 2 pgs.
"U.S. Appl. No. 18/157,504, Response filed Mar. 3, 2026 to Final Office Action mailed Dec. 11, 2025", 14 pgs.
"U.S. Appl. No. 18/157,504, Non Final Office Action mailed May 8, 2026", 21 pgs.

* cited by examiner

TECHNIQUES FOR PROCESSING CBCT PROJECTIONS

TECHNICAL FIELD

Embodiments of the present disclosure pertain generally to medical image and artificial intelligence processing techniques, including processing on data produced by cone beam computed tomography (CBCT) imaging modalities. Additionally, the present disclosure pertains to the use of such processed image data in connection with a radiation therapy planning and treatment system.

BACKGROUND

Radiation therapy (or "radiotherapy") can be used to treat cancers or other ailments in mammalian (e.g., human and animal) tissue. One such radiotherapy technique is provided using a Gamma Knife, by which a patient is irradiated by a large number of gamma rays that converge with high intensity and high precision at a target (e.g., a tumor). Another such radiotherapy technique is provided using a linear accelerator (LINAC), whereby a tumor is irradiated by high-energy particles (e.g., electrons, protons, ions, high-energy photons, and the like). The placement and dose of the radiation beam must be accurately controlled to ensure the tumor receives the prescribed radiation, and the placement and shaping of the beam should be such as to minimize damage to the surrounding healthy tissue, often called the organ(s) at risk (OARs).

In radiotherapy, treatments are delivered over a course of several fractions. Hence, patient repositioning and especially the relative position of the lesion, also known as the target, to OARs is crucial to maximize tumor control while minimizing side effects. Modern radiotherapy benefits from the use of on board imaging, especially of the widely adopted Cone Beam Computer Tomography (CBCT) systems. In many scenarios, CBCT imaging systems are built onto linear accelerators to guide or adapt radiotherapy treatment.

At a high level, usable image data is produced in a CBCT imaging system from a process of image reconstruction, which includes mapping a set of X-ray images taken during a gantry rotation around the patient to a 3D (or 4D temporally resolved) volume. Although CBCT images can be captured in a rapid manner, CBCT images may encounter high levels of scatter, motion artifacts from a long acquisition, an inherent sampling insufficiency, and data truncation from limited field of view of each projection. As a result, in a radiotherapy setting, CBCT images may not provide adequate information to fully assess a position of a tumor to be targeted as well as of the OARs to be spared.

OVERVIEW

In some embodiments, methods, systems, and computer-readable mediums are provided for accomplishing image processing by generating quantitative CBCT images based on data processing of CBCT projections with a predictive regression model. Such a regression model may be trained to receive a CBCT projection as input and produce a deficiency-corrected projection (e.g., a scatter free projection) or estimations of the deficiencies (e.g., estimations of scatter in a projection).

In some aspects, the techniques described herein relate to a computer-implemented method for training a regression model for cone-beam computed tomography (CBCT) data processing, the method including: obtaining a reference medical image of an anatomical area; generating, from the reference medical image, a plurality of variation images, wherein the plurality of variation images provide variation in representations of the anatomical area; identifying projection viewpoints, in a CBCT projection space, for each of the plurality of variation images; generating, at each of the projection viewpoints, a set of CBCT projections and a corresponding set of simulated aspects of the CBCT projections; and training the regression model, using the corresponding sets of the CBCT projections and the simulated aspects of the CBCT projections.

In further examples, training the regression model includes training with pairs of generated CBCT projections that include the simulated aspects and generated CBCT projections that do not include the simulated deficiencies; wherein the trained regression model is configured to receive a newly captured CBCT projection that includes one or more deficiencies as input, and wherein the trained regression model is configured to provide a corrected CBCT projection as output.

In further examples, the trained regression model may be adapted to correct one or more deficiencies in the newly captured CBCT projection caused by scatter, and wherein the pairs of generated CBCT projections for training include CBCT projections that include simulated scatter and CBCT projections that do not include the simulated scatter. For instance, the trained regression model may be adapted to correct one or more deficiencies in the newly captured CBCT projection caused by a foreign material, wherein the pairs of generated CBCT projections for training include CBCT projections that include simulated artifacts caused by the foreign material and CBCT projections that remove the simulated artifacts caused by the foreign material. In a further example, the foreign material is metal, wherein the CBCT projections that remove the simulated artifacts are produced using at least one metal artifact reduction algorithm.

In further examples, the trained regression model may be adapted to correct one or more deficiencies in the newly captured CBCT projection caused by beam divergence, and wherein the corrected CBCT projection is computed in parallel-beam geometry. Also in further examples, in the plurality of variation images may include a first plurality of CBCT projections generated with a first field of view, and wherein the trained regression model is configured to receive as input a second plurality of CBCT projections having a second field of view that differs from the first field of view.

In further examples, the plurality of variation images are generated by geometrical augmentations or changes to the representations of the anatomical area, wherein the projection viewpoints correspond to a plurality of projection angles for capturing CBCT projections.

In further examples, the reference medical image is a 3D image provided from a computed tomography (CT) scan, and wherein the method further includes training of the regression model using a plurality of reference medical images from the CT scan. For instance, the reference medical image may be provided from a human patient, wherein the trained regression model is used for radiotherapy treatment of the human patient. Additionally, the method may further include training of the regression model using a plurality of reference medical images from one or more prior computed tomography (CT) scans or one or more prior CBCT scans of the human patient. In other examples, the reference medical image is provided from one of a plurality of human subjects, and the method further includes training of the model using a plurality of reference medical images from each of the plurality of human subjects.

In other aspects, the techniques described herein relate to a computer-implemented method for using a trained regression model (e.g., in an inference or prediction workflow) for cone-beam computed tomography (CBCT) data processing, the method including: accessing a trained regression model configured for removing deficiencies in CBCT projections, wherein the trained regression model is trained using corresponding sets of simulated deficiencies and CBCT projections at each of a plurality of projection viewpoints in a CBCT projection space, wherein the sets of simulated deficiencies and CBCT projections are generated based on a reference medical image; providing a first plurality of CBCT projections as an input to the trained regression model, wherein the first plurality of CBCT projections include one or more deficiencies; and obtaining a second plurality of CBCT projections as an output of the trained regression model, wherein the second plurality of CBCT projections include corrections to the one or more deficiencies.

In an example, the trained regression model (used in the inference or prediction workflow) is trained with pairs of generated CBCT projections that include simulated deficiencies and generated CBCT projection images that do not include the simulated deficiencies. In some examples, the one or more deficiencies in the first plurality of CBCT projections are caused by scatter, wherein the pairs of generated CBCT projections used for training include CBCT projections that include simulated scatter and CBCT projections that do not include the simulated scatter. In other examples, the one or more deficiencies in the first plurality of CBCT projections are caused by a foreign material, wherein the pairs of generated CBCT projections used for training include CBCT projections that include simulated artifacts caused by the foreign material and CBCT projections that remove the simulated artifacts caused by the foreign material. In further examples, the foreign material is metal, wherein the CBCT projections that remove the simulated artifacts are produced using at least one metal artifact reduction algorithm.

In some examples of the inference or prediction workflow, the deficiencies in the first plurality of CBCT projections are caused by beam divergence, wherein the second plurality of CBCT projections are produced based on parallel-beam geometry. In other examples, the first plurality of CBCT projections are captured with a first field of view, wherein the CBCT projections used for training are generated with a second field of view that differs from the first field of view.

In further examples of the inference or prediction workflow, the reference medical image used for training is one of a plurality of 3D images provided from a computed tomography (CT) scan. In some examples, the reference medical image used for training is from a human patient, wherein the 3D CBCT image is used for radiotherapy treatment of the human patient. In other examples, the trained regression model is trained based on reference images captured from a plurality of human subjects.

In further examples of the inference or prediction workflow, the method includes performing reconstruction of a 3D CBCT image (or, a 4D CBCT image volume) from the second plurality of CBCT projections.

The training or usage methods noted above may be implemented as a non-transitory computer-readable storage medium including computer-readable instructions, wherein the instructions, when executed, cause a computing machine to perform the operations identified above. The training or usage methods noted above also may be implemented in a computing system comprising: a storage device or memory (e.g., including executable instructions or imaging data); and processing circuitry configured (e.g., based on the executable instructions) to perform the operations identified.

The above paragraphs are intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
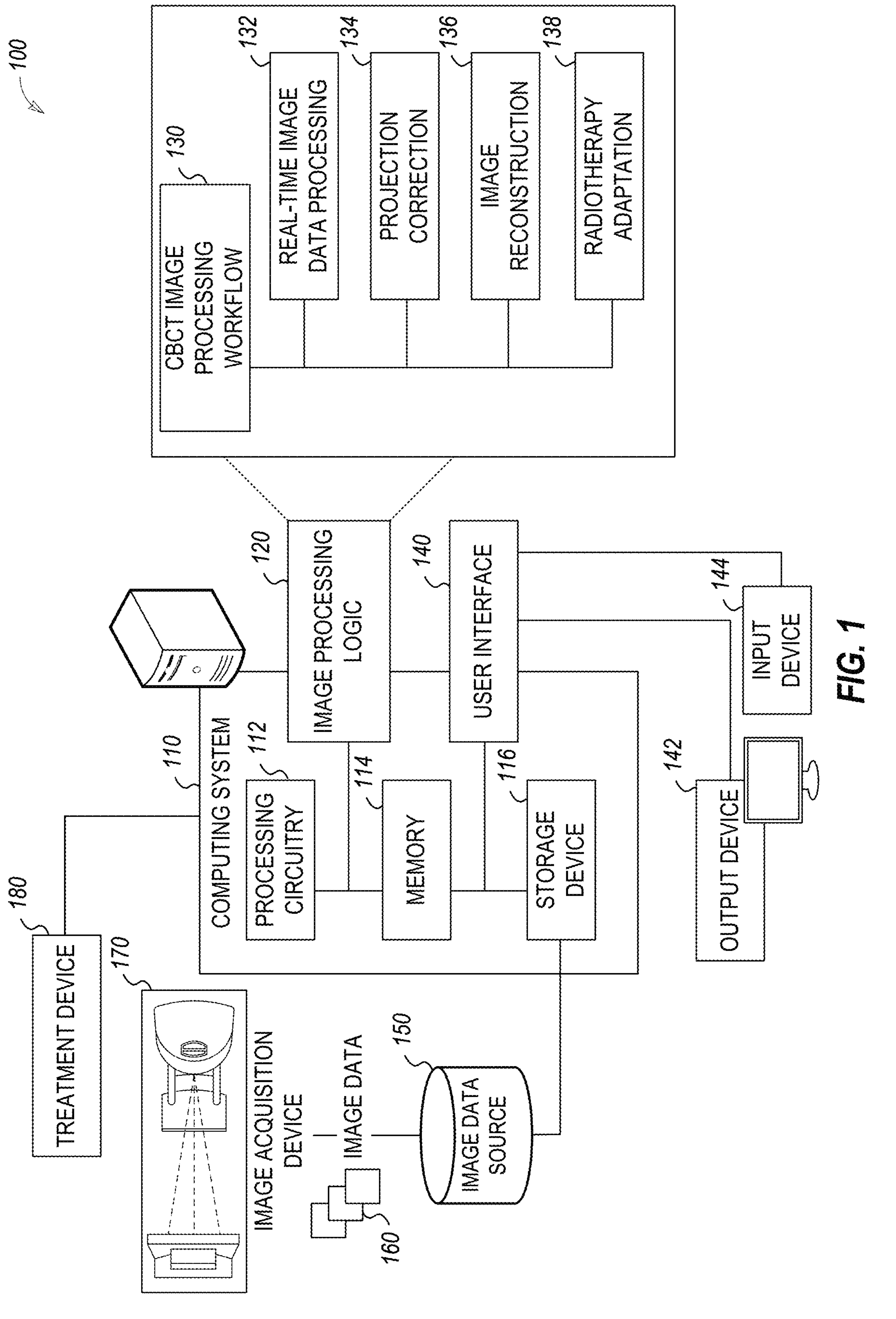
FIG. 1 illustrates a radiotherapy system, according to some examples.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not to be taken in a limiting sense, and the scope of the present disclosure is defined by the appended claims and their equivalents.

The following discusses various implementations of image processing technologies, which enable improved performance of cone-beam computed tomography (CBCT) imaging with use of an efficient, fast, and customizable deep convolutional neural network (CNN) architecture. Such processing of CBCT image data can be used to enable various use cases and treatments within radiotherapy settings. However, it will be understood that the image processing approaches discussed herein may be applicable to other medical and diagnostic imaging fields (e.g., radiology).

As is well known, CBCT images are generally of significantly lower image quality than the diagnostic CT images that are typically used for radiotherapy treatment planning. Some of the main causes of reduced image quality in CBCT images are scatter contamination, projection inconsistency, and cone-beam sampling insufficiency. Regarding scatter, cone-beam geometry has much higher patient scatter contribution than diagnostic CT geometry, which causes shading and non-uniformity artifacts in the resulting images. Regarding projection inconsistency, discrepancies from different projection lines, caused for example by beam hardening, results in noise and streak artifacts. Regarding cone-beam sampling insufficiency, CBCT acquisitions in radiotherapy typically consist of a circular arc around the patient. If a cone beam projection consisted of parallel beamlets, there would be sufficient information to fully reconstruct a 3D image. However, since the beamlets are divergent, there is insufficient data to reconstruct a 3D image without further constraints or approximations.

Various approaches have been attempted to remedy some of the issues with CBCT image capture and reconstruction. For instance, advanced physical model based reconstruction has attempted to overcome many of the limitations of CBCT capture, but can either be slow, difficult to implement in practice, or provide imperfect results when applied to real world data. Likewise, many prior techniques for applying corrections for scatter and artifacts are performed after image reconstruction, even though the image artifacts are present in individual CBCT projections before reconstruction. Higher quality CBCT imaging data is needed—ideally clinically indistinguishable from diagnostic CT—to enable such images to drive adaptive radiotherapy workflows and treatments.

Many of the following examples refer to the use of artificial intelligence technologies—such as machine learning and convolutional neural networks (CNNs)—to process CBCT imaging data. Data driven methods to process image data using deep CNNs have gained vast popularity in computational imaging due to their high accuracy and ability to infer complex phenomena from examples. However, many existing architectures are not suitable for CBCT reconstruction due to high memory or computational cost, or exhibiting dangerous instability.

In the examples discussed herein, various approaches for CBCT artifact reduction, scatter correction, and image reconstruction are provided. One example includes methods for training and usage of a projection correction model, to correct CBCT projections for deficiencies caused by scatter, cone beam artifacts, metal artifacts, and the like. Another example includes methods for training CNNs for performing enhanced CBCT image reconstruction. Each of these examples result in an input to fast reconstruction that is usable in a variety of radiotherapy settings, including during real-time adaptive radiotherapy. Additionally, the disclosed use of such enhanced CBCT image reconstruction and quantitative CBCTs may allow radiotherapy plans to be generated online in real time, and for radiotherapy plans to be generated or modified even without the need of an offline-generated plan.

The technical benefits of the following techniques include improved image quality and improved speed to develop CBCT images with reduced artifacts and improved quality. The use of such CBCT images can assist in the improved accuracy in the delivery of radiotherapy treatment dosage from a radiotherapy machine, and the improved delivery of radiotherapy treatment and dose to intended areas. The technical benefits of using improved quality CBCT images thus may result in many apparent medical treatment benefits, including improved accuracy of radiotherapy treatment, reduced exposure of healthy tissue to unintended radiation, reduction of side-effects, daily adaptation of the radiotherapy treatment plan, and the like.

The technical benefits of the following techniques are also apparent when used in an adaptive radiotherapy setting that uses CBCT images to generate new treatment plans at each fraction. In captured images, quantitative pixel values are related to physical properties of the patient that affect dose delivery. The principal quantity of interest is electron density, and atomic number plays a secondary effect. CBCT images often cannot be related to one or both of these properties in a straightforward way, which limits their value in adaptive radiotherapy. Accordingly, the following techniques improve the ability to compute a dose distribution based on CBCT images, which is in turn required for replanning based on CBCT images.

Figure 13:
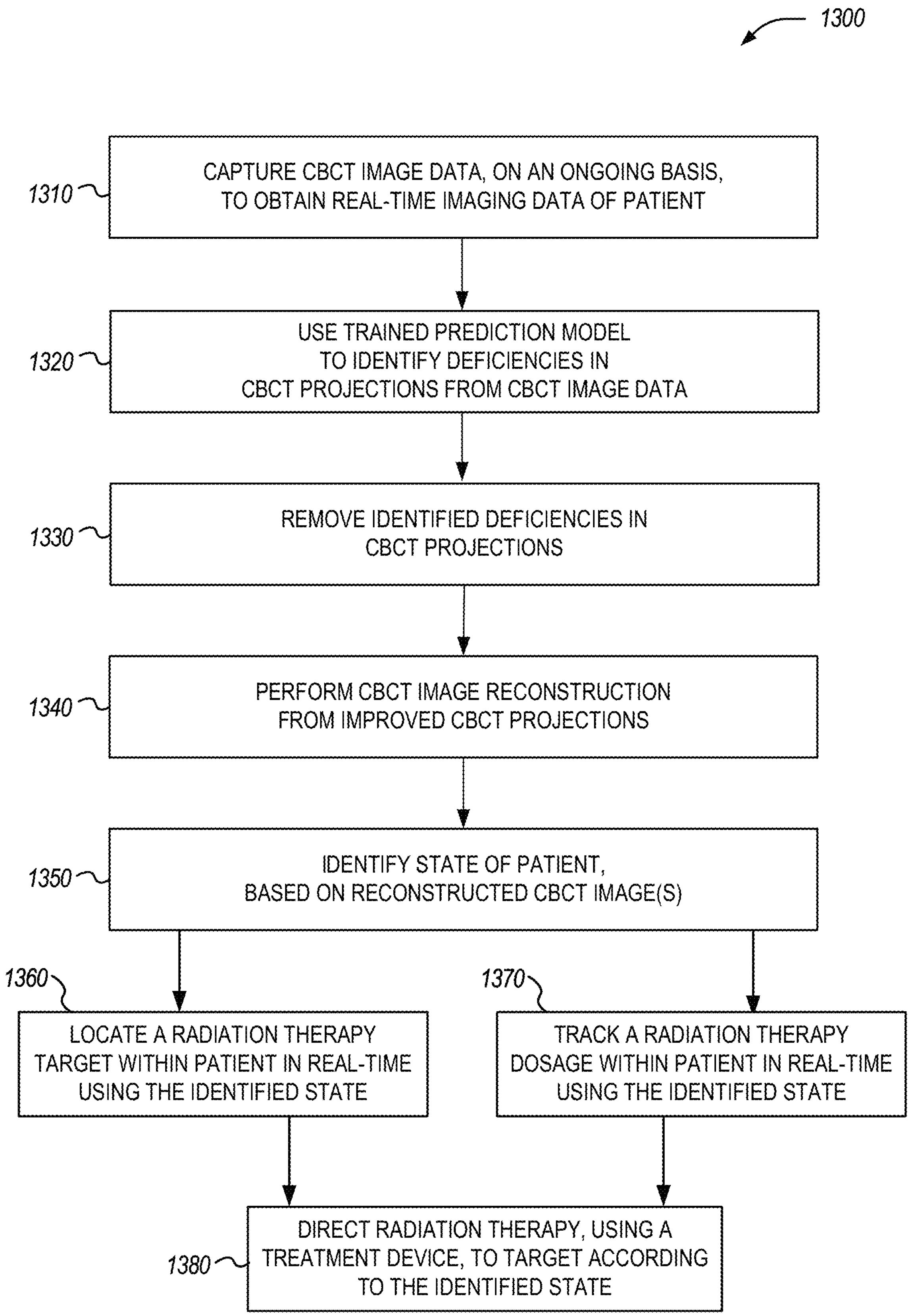
FIG. 13 illustrates a flowchart of a method performed by a computing system for image processing and artifact removal within radiotherapy workflows, according to some examples.
Figure 14:
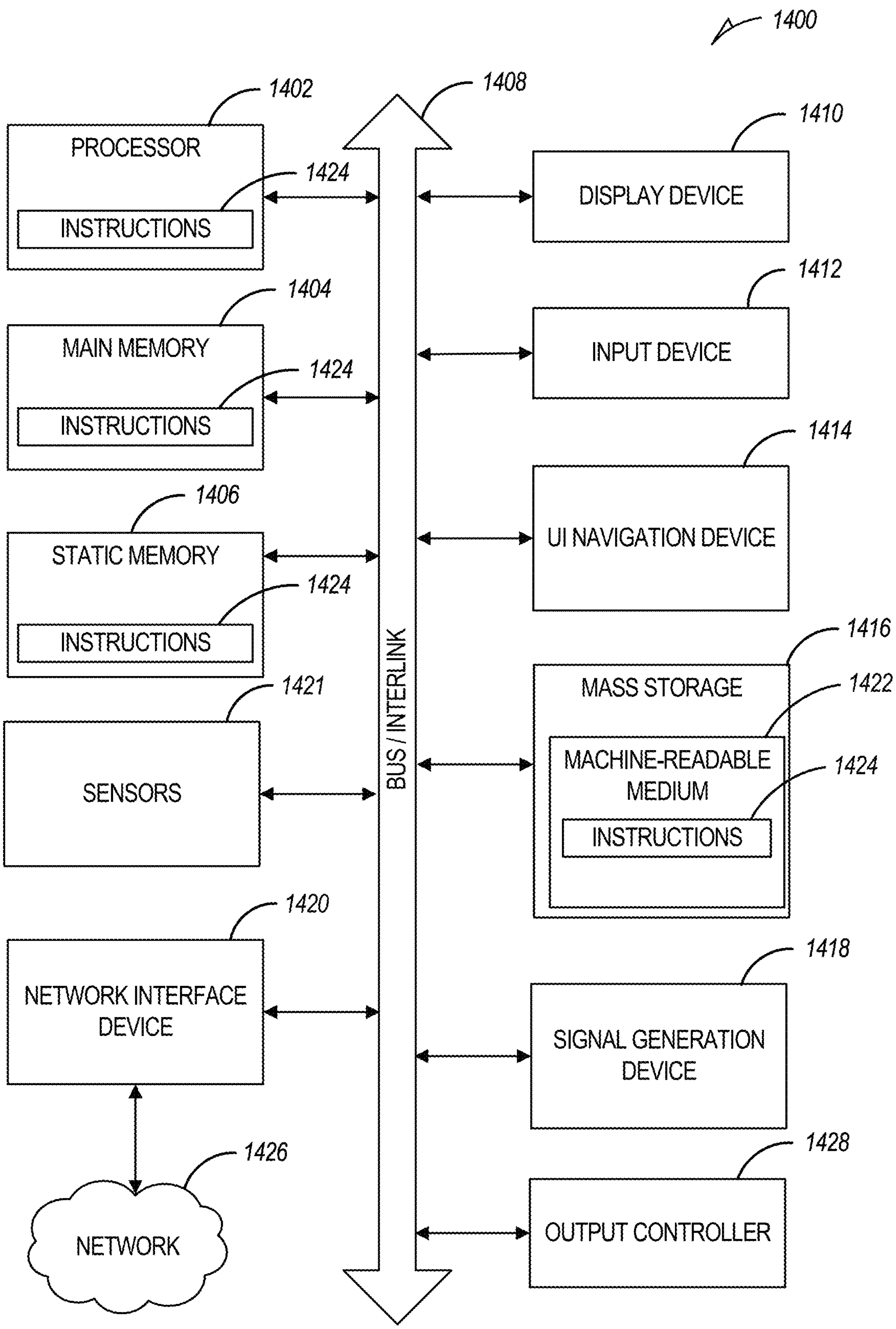
FIG. 14 illustrates an exemplary block diagram of a machine on which one or more of the methods as discussed herein can be implemented.

The following paragraphs provide an overview of example radiotherapy system implementations and treatment use cases (with reference to FIGS. 2A and 2B), including with the use of computing systems and hardware implementations (with reference to FIGS. 1 and 14). The following then continues with a discussion of workflows for processing CBCT imaging data (with reference to FIGS. 3, 5, and 8), workflows for training a machine learning model to infer and/or correct artifacts (with reference to FIGS. 4 and 6), workflows to correct specific types of artifacts with machine learning inference (with reference to FIGS. 7A to 7C), and workflows for CBCT image reconstruction (with reference to FIGS. 9 and 10). Finally, additional processing details of training and using a machine learning model for scatter and artifact correction are disclosed, including use in a radiotherapy therapy session for a particular patient (with reference to FIGS. 11 to 13).

FIG. 1 illustrates a radiotherapy system 100 adapted for using CBCT image processing workflows. The image processing workflows may be used to remove artifacts in real-time CBCT projection image data, to enable the radiotherapy system 100 to provide radiation therapy to a patient based on specific aspects of the real-time CBCT imaging. The radiotherapy system includes an image processing computing system 110 which hosts image processing logic 120. The image processing computing system 110 may be connected to a network (not shown), and such network may be connected to the Internet. For instance, a network can connect the image processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170, and a treatment device 180 (e.g., a radiation therapy device). As an example, the image processing computing system 110 can be configured to perform real-time CBCT image artifact removal by executing instructions or data from the image processing logic 120, as part of operations to generate and customize radiation therapy treatment plans to be used by the treatment device 180.

The image processing computing system 110 may include processing circuitry 112, memory 114, a storage device 116, and other hardware and software-operable features such as a user interface 140, communication interface, and the like. The storage device 116 may store computer-executable instructions, such as an operating system, radiation therapy treatment plans (e.g., original treatment plans, adapted treatment plans, or the like), software programs (e.g., radiotherapy treatment plan software, artificial intelligence implementations such as machine learning models, deep learning models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the image processing logic 120 and the user interface 140). The instructions may also reside, completely or at least partially, within the memory 114 and/or within the processing circuitry 112 during execution thereof by the image processing computing system 110, with the memory 114 and the processing circuitry 112 also constituting machine-readable media.

The memory 114 or the storage device 116 may constitute a non-transitory computer-readable medium. For example, the memory 114 or the storage device 116 may store or load instructions for one or more software applications on the computer-readable medium. Software applications stored or loaded with the memory 114 or the storage device 116 may include, for example, an operating system for common computer systems as well as for software-controlled devices. The image processing computing system 110 may also operate a variety of software programs comprising software code for implementing the image processing logic 120 and the user interface 140. Further, the memory 114 and the storage device 116 may store or load an entire software application, part of a software application, or code or data that is associated with a software application, which is executable by the processing circuitry 112. In a further example, the memory 114 or the storage device 116 may store, load, or manipulate one or more radiation therapy treatment plans, imaging data, patient state data, dictionary entries, artificial intelligence model data, labels, and mapping data, etc. It is contemplated that software programs may be stored not only on the storage device 116 and the memory 114 but also on a removable computer medium, such as a hard drive, a computer disk, a CD-ROM, a DVD, a HD-DVD, a Blu-Ray DVD, USB flash drive, a SD card, a memory stick, or any other suitable medium; such software programs may also be communicated or received over a network.

Although not depicted, the image processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber optic, USB 3.0, thunderbolt, and the like), a wireless network adaptor (e.g., such as an IEEE 802.11/Wi-Fi adapter), a telecommunication adapter (e.g., to communicate with 3G, 4G/LTE, and 5G networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the image processing computing system 110 may obtain image data 160 (e.g., CBCT projections) from the image data source 150, for hosting on the storage device 116 and the memory 114. In an example, the software programs operating on the image processing computing system 110 may convert or transform medical images of one format to another format, or may produce synthetic images. In another example, the software programs may register or associate a patient medical image (e.g., a CT image, an MR image, or a reconstructed CBCT image) with that patient's dose distribution of radiotherapy treatment (e.g., also represented as an image) so that corresponding image voxels and dose voxels are appropriately associated. In another example, the software programs may visualize, hide, emphasize, or de-emphasize some aspect of anatomical features, patient measurements, patient state information, or dose or treatment information, within medical images. The storage device 116 and memory 114 may store and host data to perform these purposes, including the image data 160, patient data, and other data required to create and implement a radiation therapy treatment plan based on artifact-corrected imaging data.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 160 to be received or obtained in memory 114, and processed using the image processing logic 120. For example, the image processing computing system 110 may receive the image data 160 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing/simulation environment that uses a network to collaboratively perform the embodiments described herein (such as in an edge computing environment). In addition, such network may be connected to the Internet to communicate with servers and clients that reside remotely on the Internet.

In further examples, the processing circuitry 112 may utilize software programs (e.g., a treatment planning software) along with the image data 160 and other patient data to create, modify, or verify a radiation therapy treatment plan. In an example, the image data 160 may include 2D or 3D volume imaging, such as from a CT or MR, or from a reconstructed, artifact-free (or artifact-reduced) CBCT image as discussed herein. In addition, the processing circuitry 112 may utilize aspects of artificial intelligence (AI) such as machine learning, deep learning, and neural networks to generate or control various aspects of the treatment plan, including in response to an estimated patient state or patient movement, such as for adaptive radiotherapy applications.

For instance, such software programs may utilize image processing logic 120 to implement a CBCT image processing workflow 130, using the techniques further discussed herein. The processing circuitry 112 may subsequently then modify and transmit a radiation therapy treatment plan via a communication interface and the network to the treatment device 180, where the radiation therapy plan will be used to treat a patient with radiation via the treatment device, consistent with information in the CBCT image processing workflow 130. Other outputs and uses of the software programs and the CBCT image processing workflow 130 may occur with use of the image processing computing system 110. As discussed further below, the processing circuitry 112 may execute a software program that invokes the CBCT image processing workflow 120 to implement functions that control aspects of image capture, projection, artifact correction, image construction, and the like.

Many of the following examples refer to the capture of CBCT projections in the image data 160, in a setting where the image acquisition device 170 is a CBCT scanner and produces cone beam CT image data. However, the image data 160 used as part of radiotherapy treatment may additionally include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 160 may also include or be associated with auxiliary information, such as segmentations/contoured images, or dose images. In an example, the image data 160 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may also comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 160 may be received and stored in any type of data or any type of format (e.g., in a Digital Imaging and Communications in Medicine (DICOM) format) that the image acquisition device 170 and the image processing computing system 110 may use to perform operations consistent with the disclosed embodiments.

In an example, the image acquisition device 170 may be integrated with the treatment device 180 as a single apparatus (e.g., a CBCT imaging device combined with a linear accelerator (LINAC), as described in FIG. 2B below). Such a LINAC can be used, for example, to precisely determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The image processing computing system 110 may communicate with an external database through a network to send and receive a plurality of various types of data related to image processing and radiotherapy operations. For example, an external database may include machine data that is information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The image processing computing system 110 can collect and obtain data, and communicate with other systems, via a network using one or more communication interfaces, which are communicatively coupled to the processing circuitry 112 and the memory 114. For instance, a communication interface may provide communication connections between the image processing computing system 110 and radiotherapy system components (e.g., permitting the exchange of data with external devices). For instance, the communication interface may in some examples have appropriate interfacing circuitry from an output device 142 or an input device 144 to connect to the user interface 140, which may be a hardware keyboard, a keypad, or a touch screen through which a user may input information into the radiotherapy system 100.

As an example, the output device 142 may include a display device which outputs a representation of the user interface 140 and one or more aspects, visualizations, or representations of the medical images. The output device 142 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D volume), or any related information to the user. The input device 144 connected to the user interface 140 may be a keyboard, a keypad, a touch screen or any type of device that a user may input information to the radiotherapy system 100. Alternatively, the output device 142, the input device 144, and features of the user interface 140 may be integrated into a single device such as a smartphone or tablet computer, e.g., Apple iPad®, Lenovo Thinkpad®, Samsung Galaxy®, etc.

Furthermore, many components of the radiotherapy system 100 may be implemented with a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the image processing computing system 110, the image data sources 150, or like components, may be implemented as a virtual machine or within a cloud-based virtualization environment.

The image processing logic 120 or other software programs may cause the computing system to communicate with the image data source 150 to read images into memory 114 and the storage device 116, or store images or associated data from the memory 114 or the storage device 116 to and from the image data source 150. For example, the image data source 150 may be configured to store and provide imaging data (e.g., CBCT or CT scans, Digital Imaging and Communications in Medicine (DICOM) metadata, etc.) that the image data source 150 hosts, from image sets in image data 160 obtained from one or more patients via the image acquisition device 170, including in real-time or near-real-time settings, defined further below. The image data source 150 or other databases may also store data to be used by the image processing logic 120 when executing a software program that performs artifact correction, image reconstruction, or related outcomes of radiotherapy adaptation. Further, various databases may store machine learning or other AI models, including the algorithm parameters, weights, or other data constituting the model learned by the network and the resulting predicted or estimated data. The image processing computing system 110 thus may obtain and/or receive the image data 160 (e.g., CT images, CBCT image projections, etc.) from the image data source 150, the image acquisition device 170, the treatment device 180 (e.g., a LINAC with an on-board CT or CBCT scanner), or other information systems, in connection with performing artifact correction and other image processing as part of treatment or diagnostic operations.

The image acquisition device 170 can be configured to acquire one or more images of the patient's anatomy relevant to a region of interest (e.g., a target organ, a target tumor or both), also referred to herein as a subject anatomical area. Each image, such as a 2D image or slice, can include one or more parameters (e.g., a 2D slice thickness, an orientation, an origin and field of view, etc.). In some specific examples, such 2D imaging data can be acquired by the image acquisition device 170 in "real-time" while a patient is undergoing radiation therapy treatment, for example, when using the treatment device 180 (with "real-time" meaning, in an example, acquiring the data in 10 milliseconds or less, although other timeframes may also provide real-time data). In an example, real-time may include a time period fast enough for a clinical problem being addressed by radiotherapy planning techniques described herein. Thus, the amount of time for "real-time" planning may vary depending on target speed, radiotherapy margins, lag, response time of a treatment device, etc.

The image processing logic 120 in the image processing computing system 110 is depicted as implementing a CBCT image processing workflow 130 with various aspects relevant to processing CBCT imaging data. In an example, the CBCT image processing workflow 130 uses a real-time image data processing 132 (e.g., raw CBCT data), from which CBCT projection images are extracted. The CBCT image processing workflow 130 also includes aspects of projection correction 134, such as determined within the trained regression model discussed in further examples below. The data provided from projection correction 134 may be used with specialized techniques of image reconstruction 136, to produce a quantitative CBCT image. Such quantitative CBCT images can be used to cause radiotherapy adaptation 138, to then to control the treatment device 180 or other aspects of the radiotherapy session.

Figure 2A:
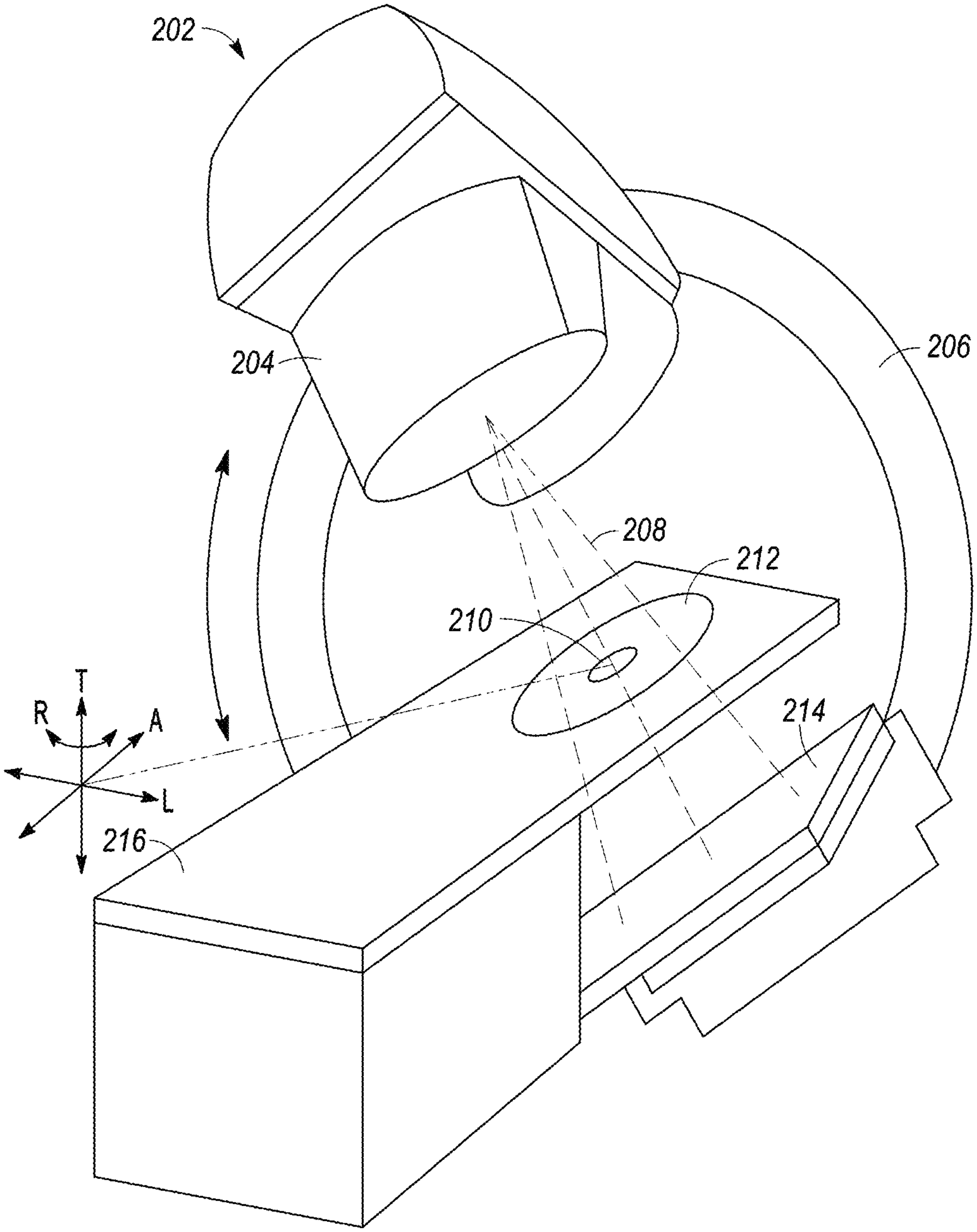
FIG. 2A illustrates a radiation therapy system having radiation therapy output configured to provide a therapy beam, according to some examples.
Figure 2B:
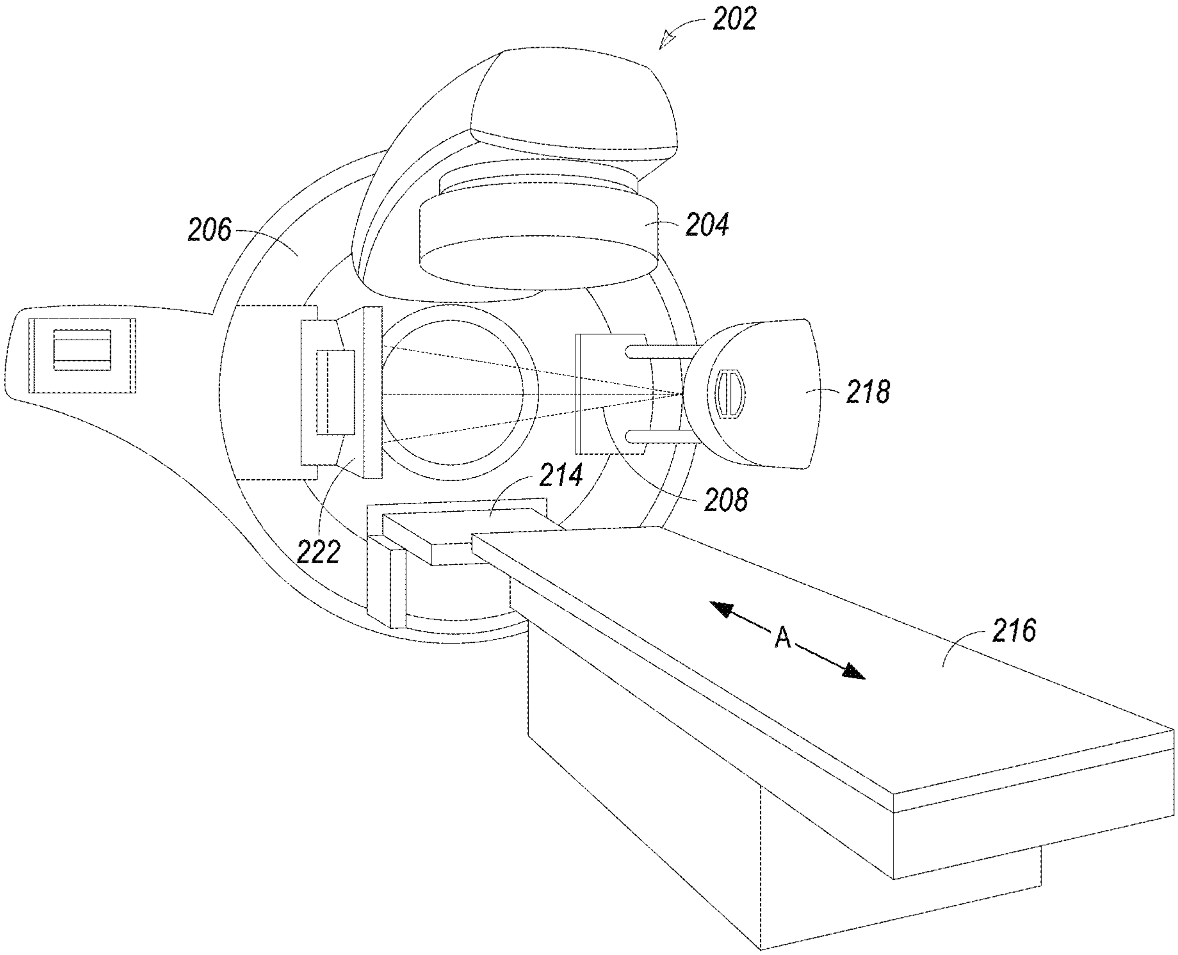
FIG. 2B illustrates a system including a combined radiation therapy system and an imaging system, such as a cone beam computed tomography (CBCT) imaging system, according to some examples.

FIG. 2A and FIG. 2B, discussed below, generally illustrate examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

FIG. 2A first illustrates a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC. A MLC may be used for shaping, directing, or modulating an intensity of a radiation therapy beam to the specified target locus within the patient. The leaves of the MLC, for instance, can be automatically positioned to define an aperture approximating a tumor cross-section or projection, and cause modulation of the radiation therapy beam. For example, the leaves can include metallic plates, such as comprising tungsten, with a long axis of the plates oriented parallel to a beam direction and having ends oriented orthogonally to the beam direction. Further, a "state" of the MLC can be adjusted adaptively during a course of radiation therapy treatment, such as to establish a therapy beam that better approximates a shape or location of the tumor or other target locus.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor precisely. The MLC may be integrated and included within gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an example, the imaging detector 214 can be located within a field of the radiation beam 208.

The imaging detector 214 can be mounted on the gantry 206 (preferably opposite the radiation therapy output 204), such as to maintain alignment with the radiation beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation beam 208 or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

FIG. 2B also illustrates a radiation therapy device 202 that may include a combined LINAC and an imaging system, such as a CT or CBCT imaging system (collectively referred to in this example as a "CT imaging system"). The radiation therapy device 202 can include an MLC (not shown). The CT imaging system can include an imaging X-ray source

218, such as providing X-ray energy in a kiloelectron-Volt (keV) energy range. The imaging X-ray source 218 can provide a fan-shaped and/or a conical radiation beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative example of FIG. 2B, the radiation therapy output 204 and the X-ray source 218 can be mounted on the same rotating gantry 206, rotationally separated from each other by 90 degrees. In another example, two or more X-ray sources can be mounted along the circumference of the gantry 206, such as each having its own detector arrangement to provide multiple angles of diagnostic imaging concurrently. Similarly, multiple radiation therapy outputs 204 can be provided.

CBCT image reconstruction is a process that takes a number of 2D x-ray projections of a patient from various angles as input to reconstruct a 3D image. In radiotherapy, the x-ray source and detector are typically mounted to the treatment gantry, orthogonal to the treatment beam. Projections are acquired while the patient is set up in treatment position. The image is then reconstructed, and the 3D CBCT image (or, 4D CBCT image) may be used for image guided radiotherapy (IGRT), i.e., shift the patient to realign the target, or adaptive radiotherapy, i.e., generate a new plan based on the new patient anatomy.

Some specific positions of tumor and OARs (and their mutually related position as a function of treatment course) as well as unusual different conditions, such as obese patients or the presence of prosthetic implants, can result in the suboptimal use of CBCT. For example, consider scenarios involving of small tumors totally embedded in soft tissue whose contrast is not clearly distinguishable from the lesion itself, or hip implants which hinder the correct localization of prostate, rectum, and bladder due to metal imaging artifacts. Historically, the problem has been solved by experience, applying the "one size fits all" strategy, potentially tailoring the performances of a CBCT system to a class of patients, e.g. obese patients with class-specific CBCT protocols. This may still result in a suboptimal image quality, because each patient might have different conditions.

Figure 3:
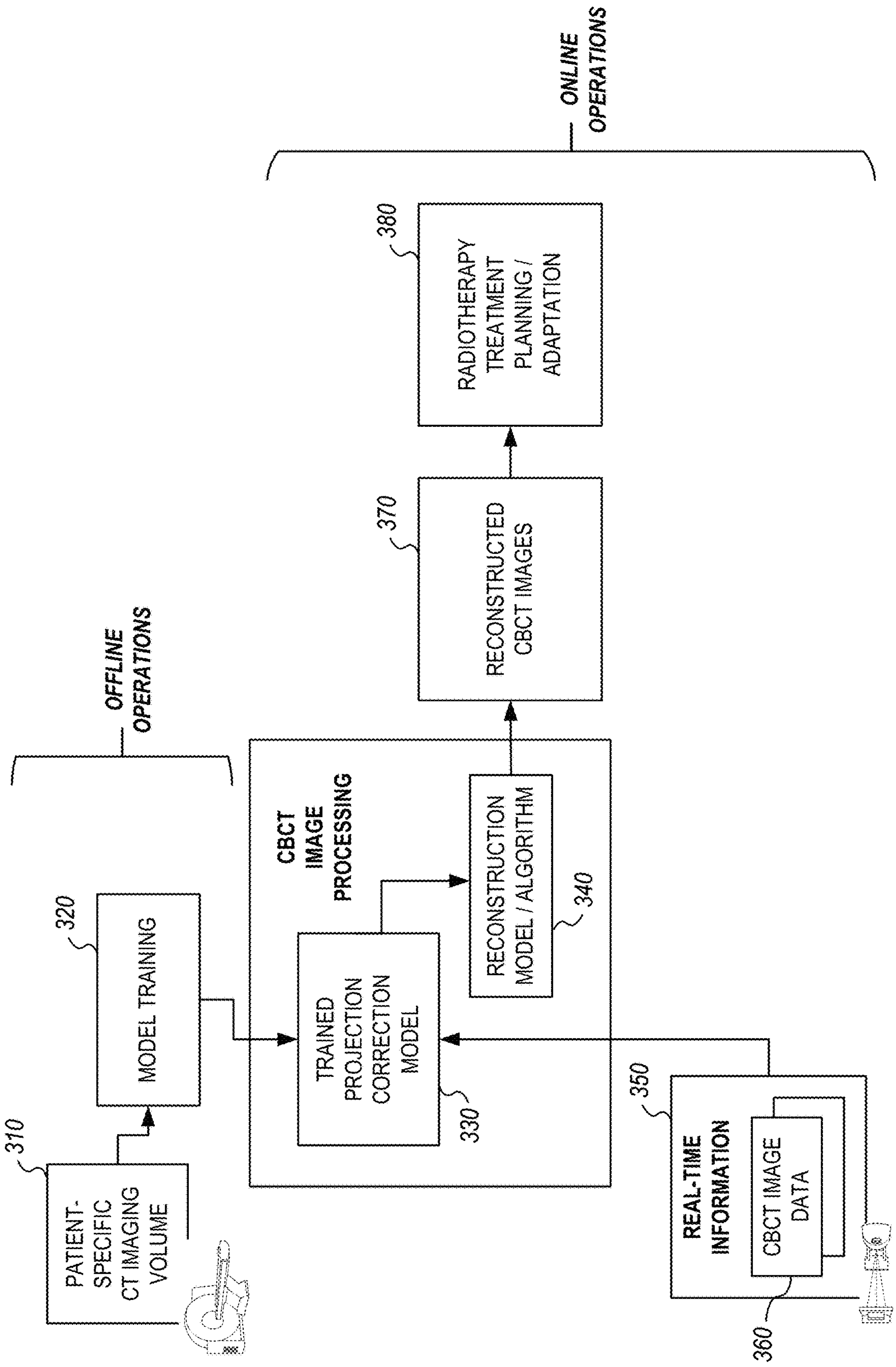
FIG. 3 illustrates a workflow for capturing and processing imaging data from a CBCT imaging system, using trained imaging processing models, according to some examples.

FIG. 3 illustrates an example workflow for capturing and processing imaging data from a CBCT imaging system, using trained imaging processing models. Here, the CBCT imaging processing includes the use of two models: a trained image reconstruction model 330, to reconstruct CBCT projections into a 3D image; and a trained artifact correction model 340 to remove artifacts from CBCT projections. It will be understood, however, that some of the examples below refer to the use of a single model—or more than two models or algorithms—to accomplish CBCT image processing.

The workflow in FIG. 3 is separated into offline operations and online operations. Offline operations are depicted as including the capture or retrieval of a patient-specific CT imaging volume 310, and the performance of model training 320. For instance, the CT imaging volume 310 may provide patient-specific data that is used with the following techniques to produce the trained projection correction model 330, which is capable of producing 2D projections with improved image quality (and, which result in fewer artifacts in the resulting reconstructed 3D CBCT image).

The online operations are depicted as including the capture of real-time information 350 including CBCT image data 360 (e.g., raw 2D projections) from a CBCT imaging modality. Projections are obtained by simulating the interaction of x-ray with the matter (patient body), and are also called DRRs (Digitally Reconstructed Radiographies). In this document, such DRRs are referred to simply as "projections" or "CBCT projections". In this example, the projections are provided to the trained projection correction model 330 and a reconstruction model 340 to produce quantitative reconstructed 3D CBCT images 370 that are artifact-reduced or artifact-free. The reconstructed 3D CBCT images 370 are then used for radiotherapy treatment planning and adaptation 380. As will be understood, the reconstruction of a 4D CBCT image may be similarly produced and used from this workflow, with a 4D CBCT image providing time-based information (e.g., respiratory motion information) based on multiple 3D CBCT volumes captured over time.

An artifact in the 3D CBCT images 370 may result from causes such as scatter, foreign material (e.g., metal), divergent beams, beam hardening, limited field of view, etc. For instance, a reconstructed 3D CBCT image may include spurious features caused by metal that are not present in the patient, resulting from the cumulative effect of combining 2D CBCT projections, each of which has been affected. With the present techniques, improved image quality—and a reduction in artifact-causing effects—is provided by the trained projection correction model 330 for individual 2D CBCT projections, leading to a reconstruction of artifact-removed or artifact-reduced 3D CBCT images.

In an example, the models 330, 340 are trained based upon pairs of image data, to identify correspondence between image characteristics and artifacts. Although the training discussed below is discussed as an offline operation, such training may be designed to operate in an online manner. Accordingly, models 330, 340 may be periodically updated via additional training or user feedback. Additionally, the particular machine learning algorithm used by the models may be selected from among many different potential supervised or unsupervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models. In the many of the examples below, a U-Net convolutional neural network is discussed, but it will be understood that other algorithms or model architectures may be substituted.

The examples below extensively discuss approaches for training a data processing model to infer and correct for deficiencies in CBCT projection data, which can address issues commonly encountered in CBCT imaging such as: cone beam artifacts caused by divergent beams, beam hardening, and limited field of view (FOV). Additional examples are provided relating to scatter estimation and removal, and compensation for the artifacts resulting from scatter. It will be understood that in the examples below, producing scatter estimations, scatter-containing projections, and scatter-free projections is but one example of how a model can be trained and used; other types of projection deficiencies (including metal artifacts, cone-beam artifacts, etc.) may also be predicted and reduced. Also, although such projection correction models may be trained and configured in a similar fashion, it will be understood that the image processing pipeline involved for scatter correction may differ from that used for correction of other types of artifacts.

Figure 4:
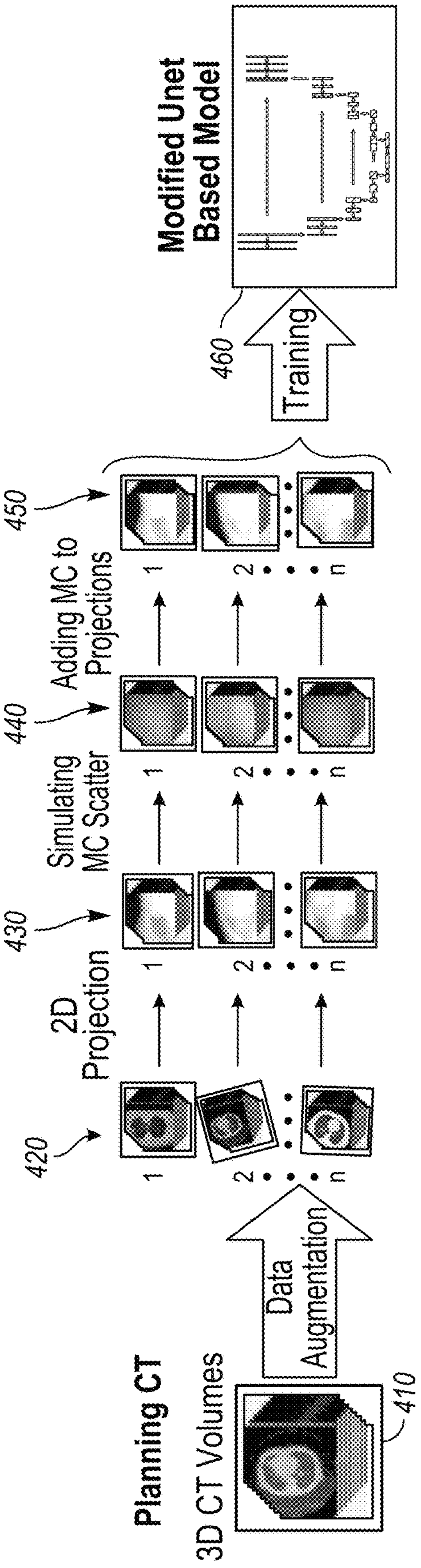
FIG. 4 illustrates a workflow for producing a trained image processing model to infer scatter in CBCT imaging data, according to some examples.

FIG. 4 illustrates a workflow for producing a trained image processing model 460 to infer scatter in CBCT imaging data. In this example, the trained image processing model 460 may provide the trained artifact correction model 340 for use in online operations as discussed in FIG. 3. Also, in this example, a workflow to infer the results of scatter is specifically discussed, but other types of artifacts and artifact correction may be implemented in the model 460 or with subsequent image reconstruction processes (e.g., as discussed with reference to FIGS. 7A to 7C, below).

In FIG. 4, the workflow for training begins with the capture of reference images within one or more 3D CT volumes 410, such as captured in offline operations (e.g., from a planning CT before a radiotherapy treatment). The reference images 420 or other imaging data from such 3D volumes 410 are used to create a series of 2D projections 430 at projection angles aligned to a CBCT projection view. In a specific example, eight different projection angles (0, 45, 90, 135, 180, 225, 270, 315) are used. However, the number of projections and the angles may differ.

Next, the 2D projections 430 are analyzed to simulate scatter such as with the use of a Monte Carlo (MC) simulated scatter function, which produces scatter estimations 440. The scatter estimations 440 are then paired with a set of corresponding projections 450, and provided for training a regression model 460. In an example, the regression model 460 is a U-net convolutional neural network.

Figure 5:
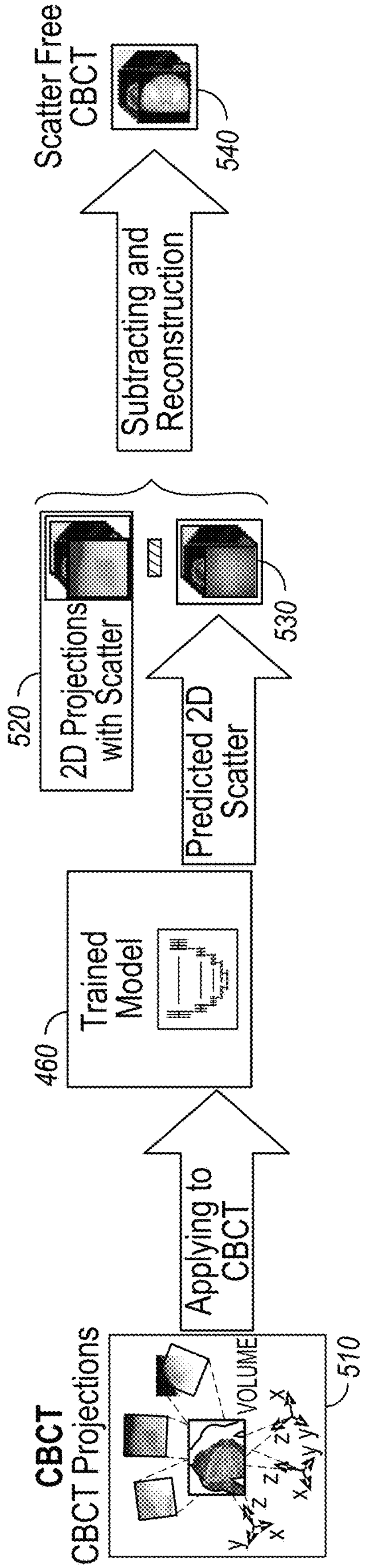
FIG. 5 illustrates a workflow for generating scatter free CBCT projections, using results of a trained image processing model, according to some examples.

FIG. 5 illustrates an example workflow for generating scatter free CBCT projections, using results of a trained image processing model. Specifically, this workflow demonstrates the use of the trained model 460 adapted for scatter prediction, as discussed above.

As shown, CBCT projections 510 are captured from a variety of viewpoints (i.e., scan angles), as the CBCT imaging modality rotates around a human patient. Such projections are provided as input to the trained model 460, which in one example is used to produce a generated set of projections 530 with predicted 2D scatter. This generated set of projections 530 is paired with a captured set of projections 520 with scatter (e.g., 2D projections extracted from the CBCT projections 510). The generated set of projections 530 is removed (e.g., subtracted) from the captured set of projections 520, and reconstructed to produce a scatter-free CBCT image 540.

Figure 6:
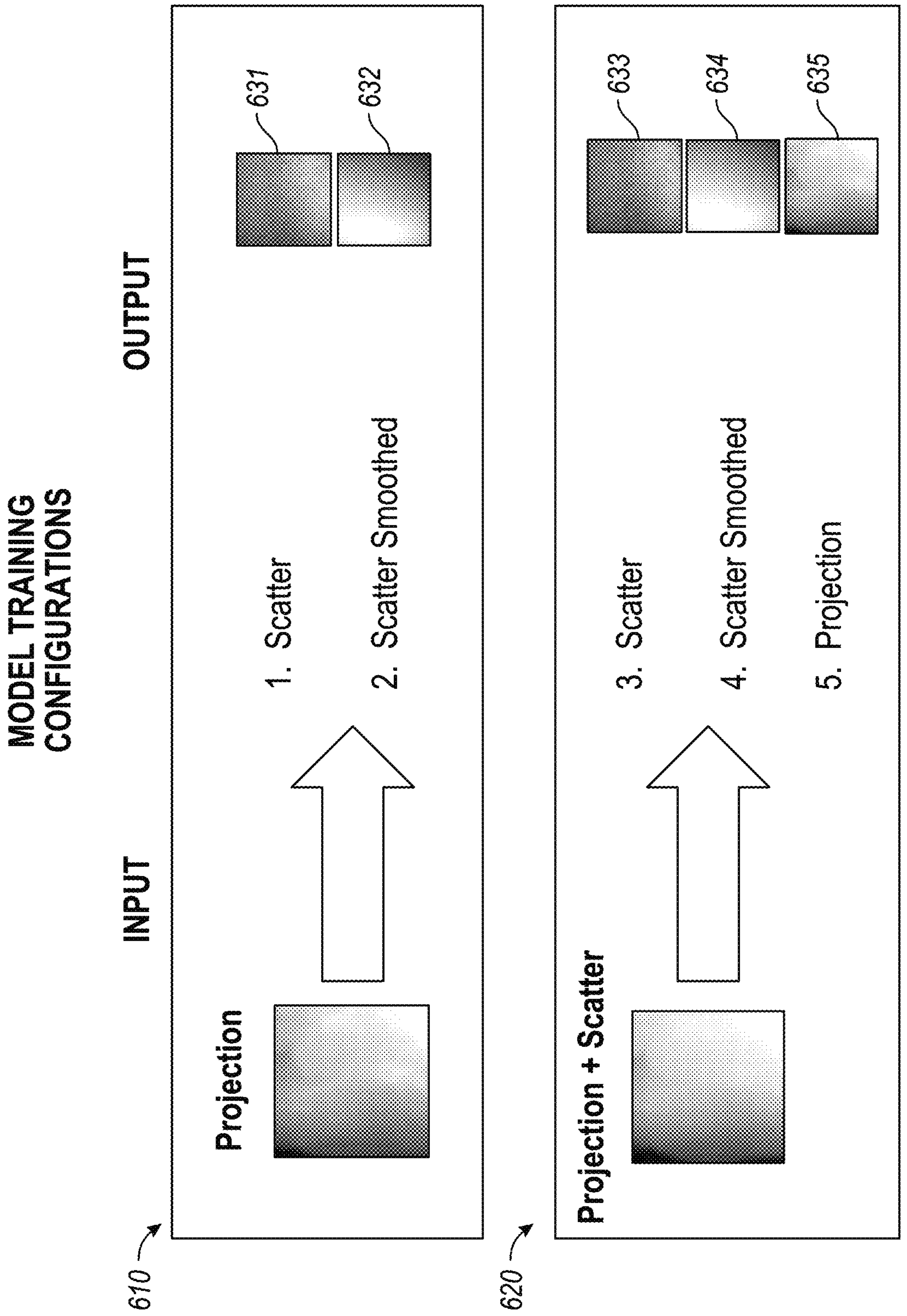
FIG. 6 illustrates approaches for training an image processing model to infer scatter in CBCT imaging data, according to some examples.

FIG. 6 illustrates example approaches for training an image processing model to infer scatter in CBCT imaging data. In a first example 610, a model (e.g., a neural network) may be trained to take projections as input to the model, and to produce an estimate of scatter 631 (e.g., inferred scatter) or smoothed scatter 632 as output. In a second example 620, a model may be trained to take projections and paired scatter for the projections as input to the model, and to produce an estimate of scatter 633 (e.g., subtracted scatter), smoothed scatter 634, or a scatter-free projection 635 (e.g., a projection image with subtracted scatter) as output. Some of the training use cases for these examples are detailed in FIGS. 7C to 7C, discussed below.

As an overview of scatter effects, consider a scenario of acquisition of a CBCT projection of a human patient. The acquisition involves x-rays emitted from an x-ray source, traveling through the patient, and reaching the detector. The detector measures signal at each pixel, but the detector does not know where this signal came from. In the case of conventional CBCT reconstruction algorithms, an assumption is made that the signal traveled a straight line connecting the source and the measuring pixel. This is commonly referred to as the "primary" signal (i.e., the signal from primary x-ray beams). In practice, however, the interaction of radiation with matter is much more complex, and there is a whole cascading 'shower' of x-ray photons generating electrons, generating x-rays photons, etc., each potentially changing direction at each interaction. Thus, CBCT projections also include a "scatter" signal (i.e., the signal from secondary or scattered x-ray beams), which includes everything other than the primary signal, for example photons that were not originally aimed at a particular pixel but changed directions and ended up adding to the total signal at the given pixel.

As will be understood, some approaches are currently used for correcting scatter from CBCT image data, with limited success. For example, some simple algorithms for CBCT artifact correction used in the radiotherapy space take raw measured Xray intensity Iraw, estimate the scatter contribution Iscat, and subtract the two to obtain a corrected projection Icor=Iraw−Iscat. Similarly, some reconstruction methods, such as the popular method by Feldkamp-Davis-Kress (FDK), assume a linear model and that is applied to the linearized projection Pcor=−log(Icor)=−log(Iraw−Iscat). The estimate of Iscat in these simple algorithms is generally not sufficient for accurate reconstruction, and can even produce instabilities in taking the logarithm (e.g., when Iscat>Iraw).

Another prior approach is to first reconstruct an 'approximate' image, and simulate realistic scatter contributions Iscat for each projection angle. This can be performed, for example, by modelling radiation transport through an approximate patient image and the detector using a Monte Carlo or a Boltzmann solver approach. However, such approaches are often not successful due to a) additional computation time due to the need to generate a first approximate image; b) additional computation time from simulating Iscat for each projection; c) inaccuracies introduced through estimating scatter on an approximate image; and d) the failure to provide inline scatter correction, due the necessity of acquiring all projections to reconstruct a first approximate image prior to estimating scatter.

Another category of prior approaches uses Artificial Intelligence (AI) to estimate scatter. These approaches are based on first generating a training dataset having paired Praw=−log(Iraw) and Iscat data, training a network with this dataset, and using the network to estimate Iscat from Praw for each projection. Such networks are often trained on a large population of patient data. Once the network is trained, Praw is used to estimate Iscat for each projection, and then Pcor=−log(Iraw−Iscat) is used to find the new 'scatter-free' projections. These approaches also may not be successful due to the large database of patient data required for each anatomy of interest and specific imaging conditions of interest. Further, it may be difficult to ensure that the training data is representative of the actual patient under study.

CBCT image reconstruction algorithms typically assume that the signal is purely the primary component, so it is beneficial to subtract the scatter component and estimate the scatter reaching the detector. Scatter cannot be measured directly, so theoretical calculations (simulations) are used to estimate its effects. As noted above, for example, Boltzmann solver or Monte Carlo techniques can be used to simulate the complex cascades of photons/electrons (and other particles) in matter. To model scatter accurately in an imaging setting, a model of the x-ray source (including any filters), the patient (e.g. with a CT), the treatment couch and any other apparatus in the path of the beam, and the detector, is used. Using this model, a simulation is created of the signal reaching each virtual pixel in the detector, to know whether the pixel is considered 'primary' or 'scatter'. This produces a total image (P+S), from primary image P and scatter image S.

When a new, real-world projection is acquired during CBCT imaging, the total image is measured. If the theoretically expected proportion of scatter is simulated for the given geometry (considering the source/patient/detector), such simulated scatter can be "subtracted" to produce an estimation of the primary image only. This estimation of the primary image can then be used in the CBCT reconstruction algorithm, which is expecting a primary signal only. The approaches discussed herein train a network (e.g., a regression model) to produce the scatter simulations. Such a network can be trained with a population-based approach, a patient-specific approach, or some mix of the two.

In a specific example applicable to a radiotherapy setting, the patient-specific approach is used to acquire a planning CT image (e.g., before the first radiotherapy treatment). This planning image is transformed by simulating many potential variations of that image (e.g., shifts, rotations, deformations). Once all of the potential variations of what the patient 'might' look like on any given day, a simulation algorithm (e.g. Monte Carlo) can be used to simulate various projection images through the planning CT image, and train a model with such projection images. Additional techniques may be applied to mix simulations with real-world measurements, model other effects, and calculate the scatter depending on the signal chain (e.g., with use of various filters, saturation, signal degradations in the detector, etc.). Thus, the total image—including the scatter component and the primary component of the image—can be simulated via a trained model.

The model may be trained to be able to calculate one based on the other (e.g. scatter signal based on total image, or primary signal based on total image). Thus, depending how the network is trained, each time a captured 'total' projection image is produced, the network can convert this data into a scatter image (e.g., an image representing the estimated scatter elements) or convert this data into a primary image (e.g., an image representing the primary x-ray). If the data is converted into a scatter image, then the scatter can be removed from the captured image (e.g., by subtracting directly, or subtracting via a logarithmic subtraction) to produce the primary image. Once the primary (e.g., scatter-corrected) image is produced for a projection, then the projection can be used directly in a typical CBCT reconstruction algorithm (e.g., in an algorithm using a typical scatter-free assumption).

Figure 7A:
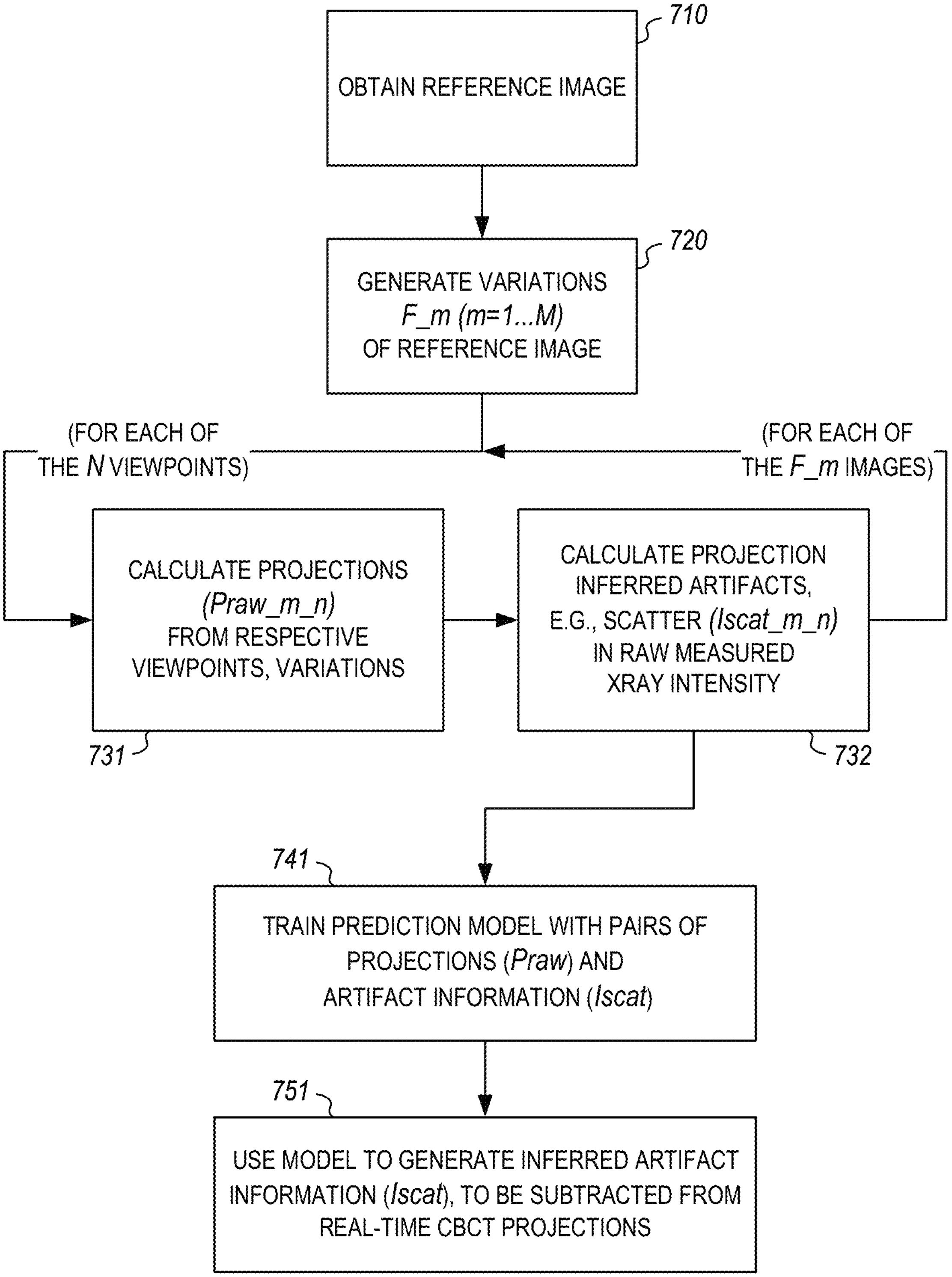
FIG. 7A illustrates an aspect of training an image processing model to generate inferred artifacts from CBCT imaging data, according to some examples.

FIG. 7A illustrates an aspect of training an image processing model to generate inferred artifacts from CBCT imaging data. In particular, this approach of training a neural network can be performed using patient-specific data, with as little as a single reference image (F_0) of that patient. For instance, consistent with the examples, above, the reference image may be obtained from a diagnostic CT scan used for radiotherapy treatment planning. In some examples, more than one reference image is used, for example if multiple images are available from different studies, or if a 4D image is acquired, where each 3D image from the 4D dataset is included as a separate image.

At operation 710, the image is obtained, and used at operation 720 to generate many variations of F_m from m=1 . . . M. For instance, such variations may be representative of anatomical changes of the patient. For each of the F_m images, the scatter component of projections Iscat_m_n and the raw projections Praw_m_n are calculated, where n=1 . . . N represents different projection viewpoints.

Once all of the training data has been generated, paired Praw and Iscat information is used as patient-specific training data to train a regression model, at operation 741. Later, during the radiotherapy treatment itself, Praw data is collected from the patient, in the form of real-time projections. The model can be used, at operation 751, to generate inferred artifact information, specifically in this example, scatter contribution (Iscat). The inferred scatter information is subsequently subtracted from raw measured Xray intensity (Iraw) to form the corrected 'scatter-free' projection: Pcor=−log(Iraw−Iscat).

Accordingly, with the approach of FIG. 7A, a regression algorithm is trained that generates scatter-free projections from measured 'raw' projections without the need for additional 3D image from that patient, although more can be added if desired. In an example, regression is performed using a U-Net convolutional neural network. However, other machine learning algorithms may be used. Additionally, a variety of algorithms or processing approaches may be used for generating the projections, such as with Monte Carlo simulations as discussed above. Also in an example, variations of F_m are generated (at operation 720) by shifting and rotating the image by various amounts in each of the degrees of freedom. This can be performed by using uniform increments on a grid, or by sampling from a probability distribution which is either uniform or representative of shifts and rotations that would be expected in practice. Optionally, deformations may be introduced.

Figure 7B:
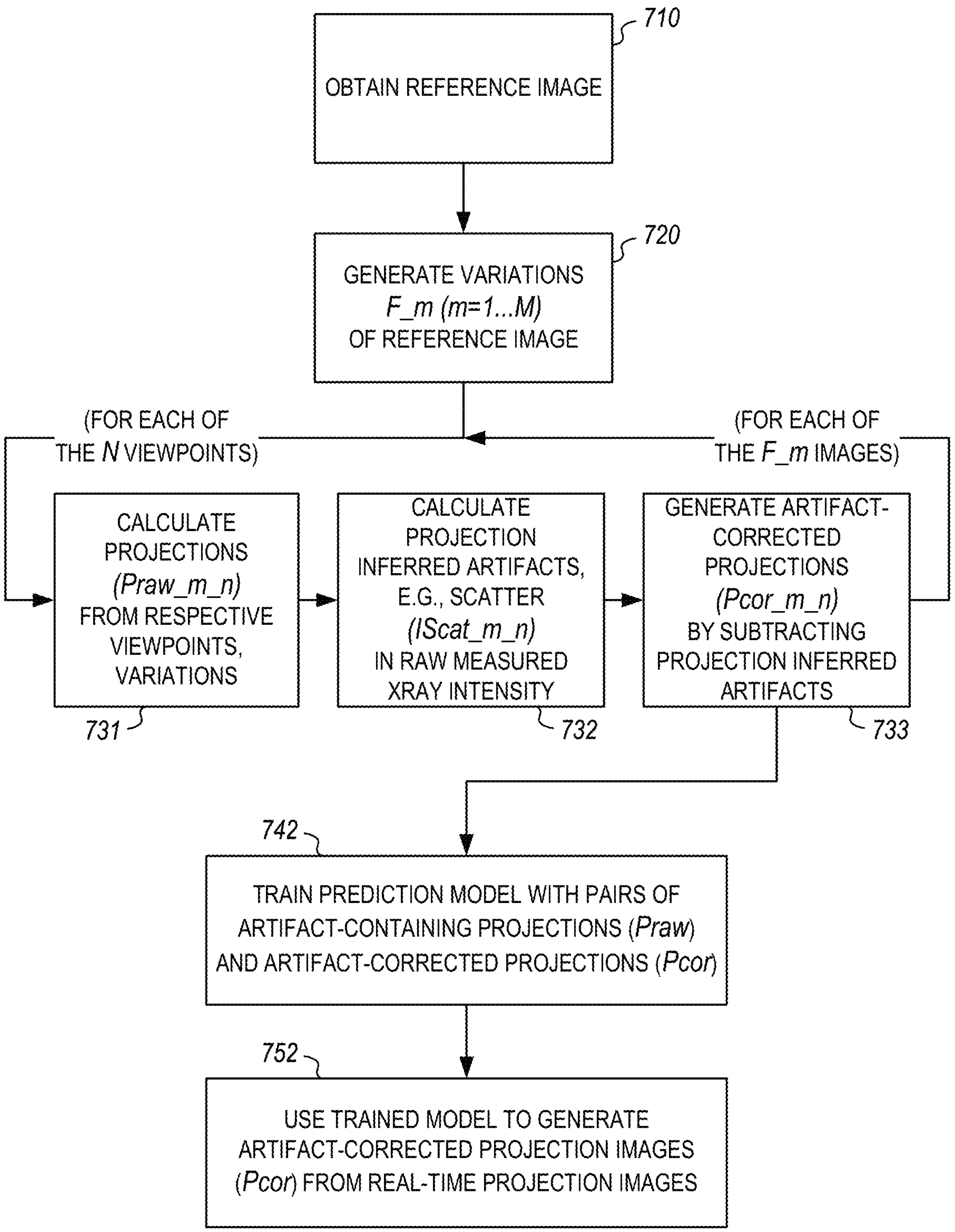
FIG. 7B illustrates an aspect of training an image processing model to generate artifact corrected images in CBCT imaging data, according to some examples.

FIG. 7B illustrates an aspect of training an image processing model to generate artifact corrected images from CBCT imaging data. This workflow is similar to the flow depicted in FIG. 7A, except that instead of training the regression model with paired Praw and Iscat data, the regression model is trained with Praw and Pcor data (at operation 742). Thus, rather than using scatter projections as an intermediary, the regression is trained to calculate the corrected data directly from the raw measured data, allowing a trained model to generate artifact-corrected projections from real-time projections (operation 752). Accordingly, this workflow can be used in addition or as a modification to prior AI-based scatter methods, such as those which involve AI population-based approaches.

With the approach in FIG. 7B, the implied scatter between the non-linear relationship between input and output of the network: i.e., Iscat=exp(−Praw)−exp(−Pcor) can be extracted (with Praw, Iscat, and Pcor produced at operations 731, 732, 733 respectively). From here, Iscat can be used directly as in the example of FIG. 7A correct the original measurements. One benefit of this approach is that the network training data need not be at the same resolution as the detector. Further, since scatter is an inherently low frequency signal, applying an AI approach to lower resolution training pairs can achieve superior computational performance. Further, the implied scatter can be implemented in various aspects of image post-processing, for example with filters (e.g. Gaussian low-pass filter) and can be intensity matched to the measurements for consistency and stability. In further examples, Pcor (e.g., produced from the workflow of FIG. 7B) can be used directly from the network output as input for reconstruction. This may offer an advantage in achieving a scatter correction as well as estimation, avoiding the naïve subtraction and potential instability from the logarithm linearization step.

The approach depicted in FIG. 7B, for training an image processing model, may be specifically used to correct cone beam artifacts in CBCT imaging data. In such an example, the training dataset is established with Praw and Pcor data, but with the Pcor data being computed in a parallel-beam geometry rather than a divergent beam geometry. This is performed for each P_m_n by ray-tracing parallel beam geometry through the images F_m. After training with this data, each measured Praw can be converted to a scatter-free, divergence-free beam. The resulting 3D image can then be reconstructed from projections that are both scatter free and in parallel-beam geometry, thus eliminating not only scatter but also cone beam artifacts.

The approach depicted in FIG. 7B, for training an image processing model, also may be extended to model physical non-linearities of an imaging system using CBCT imaging data. For example, other physical non-linearities of the imaging system may be represented in the training data input, resulting from issues such as: beam-hardening from polyenergetic source and energy dependent Xray attenuation; glare from scatter within the detector; saturation effects; lag from finite response rate of the detector and afterglow corrupting subsequent measurements; variations in gain over detector area from different sensor banks; or presence of objects in the beam path such as bow-tie filter or anti-scatter grid. The output then includes a linear projection of some quantity of interest: attenuation coefficient at a nominal energy, mass density, relative electron density, proton stopping power ratio, etc. Projections corrected in this way could be used to reconstruct quantitative CBCT images in a variety of settings. For instance, a variety of reconstruction algorithms could be used to achieve non-linear quantitative reconstruction, including fast linear algorithms such as FDK or regularized least-squares iterative.

Figure 7C:
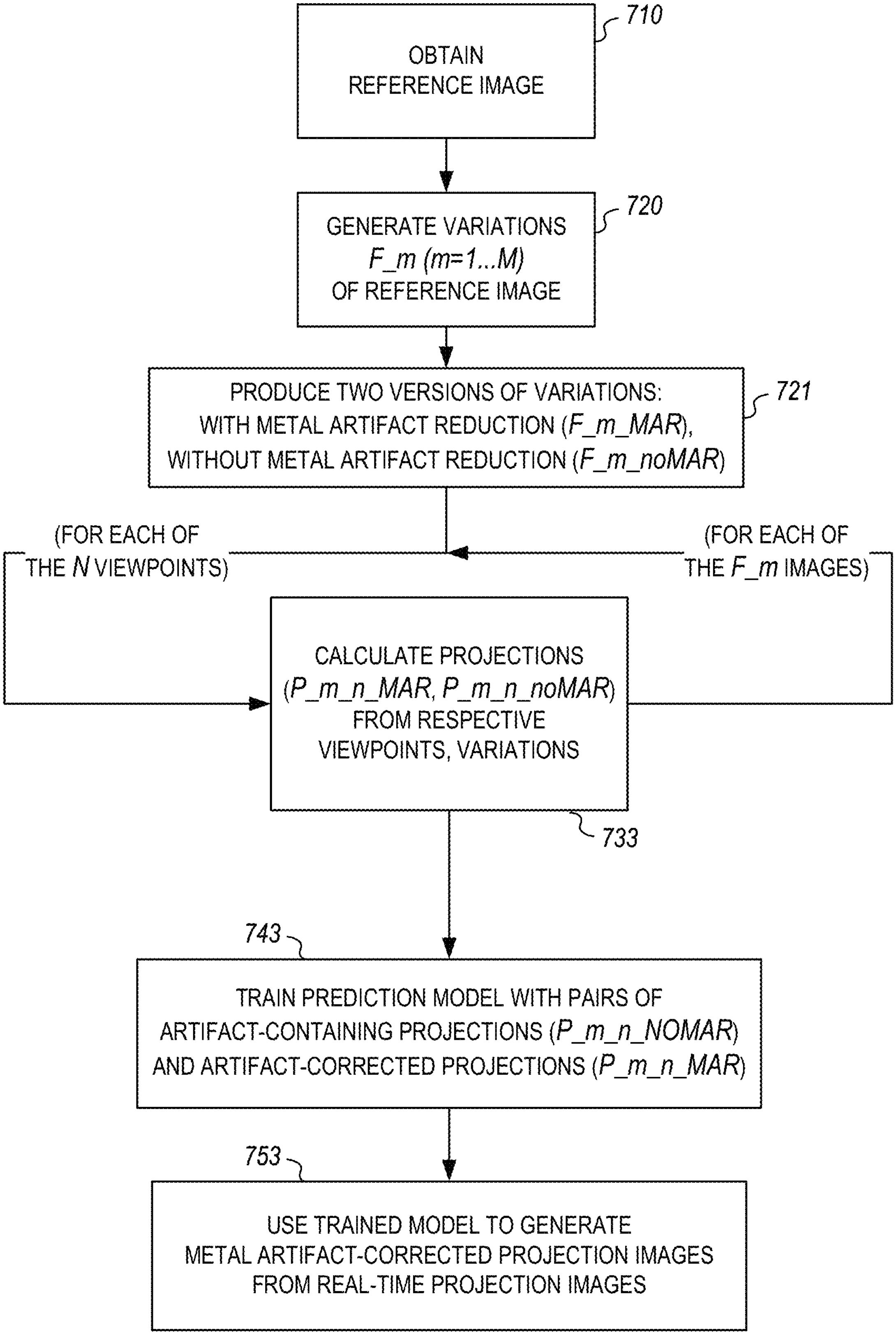
FIG. 7C illustrates an aspect of training an image processing model to correct metal artifacts in CBCT imaging data, according to some examples.

FIG. 7C illustrates an aspect of training an image processing model to correct metal artifacts in CBCT imaging data. In some cases, metal artifacts may cause artifacts in images due to their high atomic number (Z). Metal artifact reduction (MAR) algorithms can reduce these artifacts, but are often limited to removing artifacts from diagnostic CT images rather than from CBCT images.

The workflow discussed above for FIGS. 7A and 7B may be adapted for training a regression model for metal artifact reduction of CBCT projections. Specifically, for each variation of the reference image F_m, two versions can be generated, at operation 721: a first version with application of the MAR algorithms (producing image F_m_MAR), and a second version without application of the MAR algorithms (producing image F_m_noMAR).

At operation 733, projections P_m_n_MAR are generated from F_m_MAR and projections P_m_n_noMAR are generated from F_m_noMAR. The network of the regression model is trained at operation 743 using paired P_m_n_MAR and P_m_n_noMAR. The trained network then may be used at operation 753 to generate projections with MAR, when provided with new projections during real-time imaging (i.e., projections that may have metal artifacts).

Finally, any of the approaches discussed above for training an image processing model may be extended to correct for a limited field of view (FOV) in CBCT imaging data. For example, intensity data may be acquired with a limited FOV, either due to physical constraints or to reduce dose. In an example (which can be combined with the other training examples discussed above), training dataset 'raw' data is generated using a small FOV, whereas 'corrected' data is generated with a full FOV. In this manner, an algorithm can be used to automatically compensate for small FOV projections.

Figure 8:
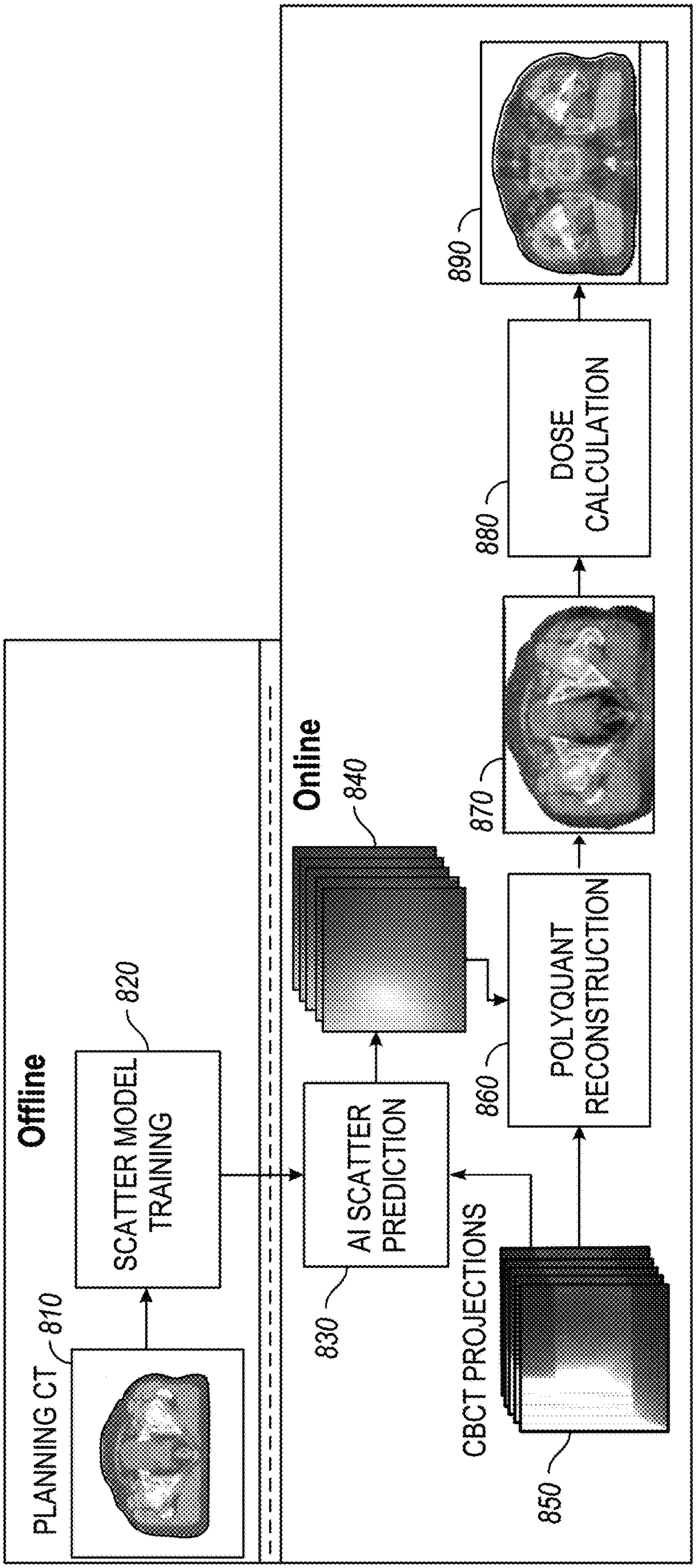
FIG. 8 illustrates a comparison of offline and online processing for scatter correction in a radiotherapy workflow, according to some examples.

FIG. 8 illustrates offline and online operations for scatter correction in a radiotherapy workflow. Similar to the approaches discussed in FIG. 3, the offline operations includes training of a model, specifically scatter model training 820, based on a reference image, specifically a planning CT image 810. Such a reference image may be taken from a larger CT volume and used to generate various projections from respective projection viewpoints, as discussed in the techniques above.

During online image processing, AI scatter prediction 830 is performed on CBCT projections 850. In an example, the estimated scatter 840 is used by a polyquant iterative reconstruction process 860, to remove the scatter as multiple projections are reconstructed into an image. In an example, the polyquant iterative reconstruction process 860 includes polyenergetic (beam hardening) and quantitative reconstruction (directly mapping into electron density). Such a process provides an integrated beam hardening model, which is dependent on materials and not the scanner. In other examples, polyquant iterative reconstruction provides quantitative reconstruction into: relative electron density (RED), mass density, monoenergetic attenuation, proton stopping power ratio, etc. As will be understood, for polyquant iterative reconstruction to successfully work, the use of an accurate x-ray spectrum, detector response, and accurate scatter estimate is required. Additional details on polyquant and qualitative iterative reconstruction is provided by Mason et al., "Quantitative cone-beam CT reconstruction with polyenergetic scatter model fusion", *Physics in Medicine & Biology* (2018), and Mason et al., "Polyquant CT: direct electron and mass density reconstruction from a single polyenergetic source", *Physics in Medicine and Biology* (2017c). Other types of image reconstruction algorithms may be used, including other types of iterative or AI-based reconstruction.

The result of the polyquant iterative reconstruction process 860 is a CBCT image 870, which may be used or adapted for further radiotherapy processing. For instance, dose calculation 880 may be performed from the CBCT image to generate a dose mapping 890 of an anatomical area relative to a radiotherapy plan.

The approaches discussed above may be integrated into CBCT image reconstruction to enable scatter reduction and a variety of other artifact improvements on raw data. Typically, image reconstruction for CBCT is a time-consuming image processing step (e.g., even taking multiple minutes) that can significantly impact steps derived from the resulting images, such as patient (re)positioning or radiotherapy plan adaptation. Hence, there is the need to guide the reconstruction process to optimize image quality for a specific patient (for instance, obese patients, prosthesis implanted patients) while skipping multiple time-consuming reconstructions by trial and error. Adaptation of Artificial Intelligence (AI) technologies, with its natural advantage of predictions and inferencing, provides a useful answer to such needs.

Figure 9:
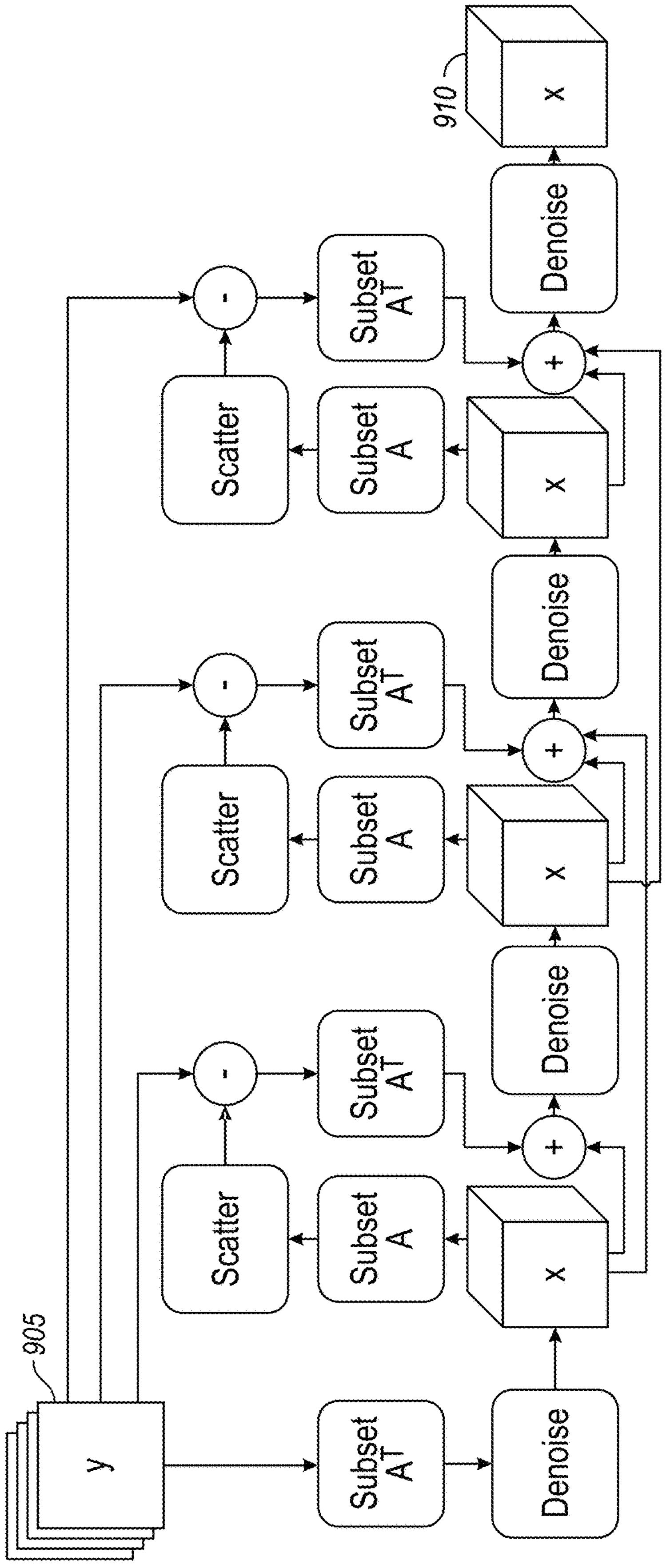
FIG. 9 illustrates an architecture for performing iterative reconstruction through measurement subset convolutional neural networks (CNNs), according to some examples.

FIG. 9 depicts an architecture for performing iterative reconstruction through measurement subset CNNs. Specifically, this architecture enables a reconstruction and correction of 2D CBCT projections (e.g., scatter corrected CBCT projections) which are de-noised and scatter-reduced, to create a resulting CBCT 3D image 910.

Figure 10:
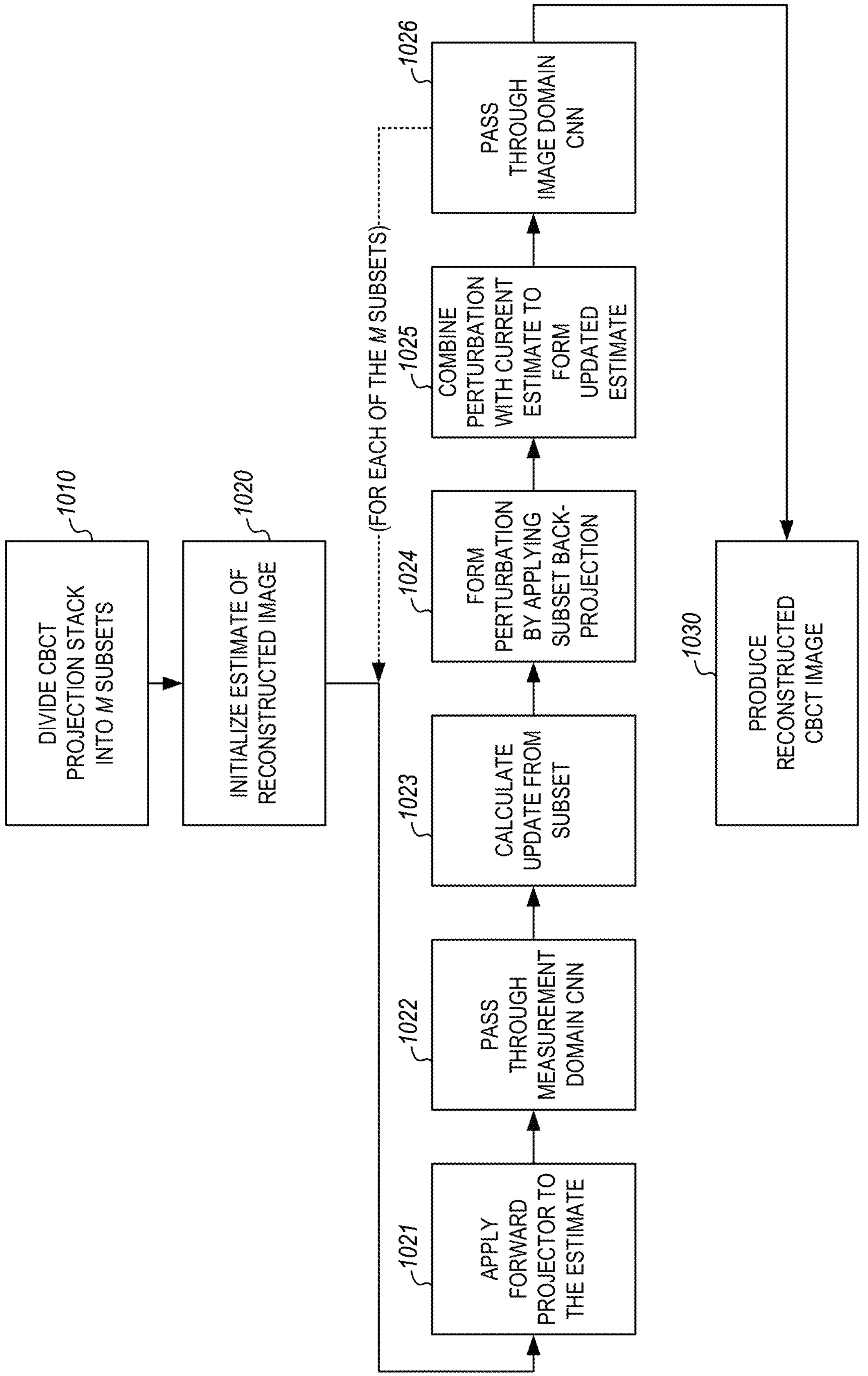
FIG. 10 illustrates a flowchart of an example method for iterative reconstruction, corresponding to the architecture of FIG. 9, according to some examples.

FIG. 10 depicts a corresponding flowchart of an example method for iterative reconstruction, using CBCT X-ray projections received from an acquisition system. It will be understood that other reconstruction approaches or algorithms may be used for reconstruction as referenced herein.

At operation 1010, the projection stack is divided into M subsets where 1≤M≤N with N the total number of projections.

At operation 1020, an estimate of the reconstructed image is initialized.

Then, for each of the M subsets, the following operations are performed:

At operation 1021, apply subset forward projector to the estimate.

At operation 1022, pass through a measurement domain CNN.

At operation 1023, calculate update from measurement subset.

At operation 1024, form perturbation by applying subset backprojection to update.

At operation 1025, add perturbation to current estimate to form new estimate.

At operation 1026, pass through an image domain CNN.

Based on the operations performed on the subsets, a reconstructed 3D CBCT image is reproduced at 1030.

The architecture and operations may be varied as follows. In a first variation, the input may be scatter contaminated and the target may be scatter corrected (for example with Monte Carlo simulation), whereby the network could infer how to correct for scatter. Other physical corrections could also be applied to the target such as beam-hardening, metal artefact, or ring correction.

In further examples, one or more previous update volumes may be combined to mimic "momentum" in classical gradient descent optimization. The weighting to accumulate these can either be a fixed parameter or trainable. Likewise, noisy but statistically independent input and scatter corrected target pairs may be used, similar to an "nosie2inverse" model, to avoid requiring a ground truth.

In further examples, the reconstruction method may be extended to four dimensions by either binning the projections or targets (e.g. into respiratory phases). Additionally, the reconstruction method may perform implicit motion compensation by having a static target and dynamic projections, whereby the network could infer motion compensation in its mapping to measurement space.

The following flowcharts discuss specific workflows for training and usage of a predictive regression model for identifying (or correcting) deficiencies or similar incomplete information in CBCT projections. Such deficiencies, in various examples, may be caused by divergence, scatter, non-linearities, or limited field-of-view. Resulting projections may include one or more of these deficiencies, or other issues not enumerated.

In a first specific aspect, a model (e.g., neural network) is trained based on a single patient-specific patient dataset, such as a planning CT, to infer divergence-free projections from divergent projections. The use case of this trained model may include, for each CBCT projection, to use the model to infer divergence-free projections and then reconstruct a 3D CBCT image with divergence-free projections. Additionally, this use case may further include creation of a 4D CBCT image volume from multiple reconstructed 3D CBCT images.

In a second specific aspect, the model (e.g., neural network) is trained based on a single patient-specific patient dataset, such as a planning CT, to infer nonlinearity free projections from raw projections. Non-linearities may include, for example, beam hardening from polyenergetic source ad energy dependent x-ray attenuation; glare from scatter within the detector; lag from finite response rate of the detector; and afterglow corrupting subsequent measurements; variations in gain over detector area from different sensor banks or presence of objects in the beam path such as bow-tie filter or anti-scatter grid. The use case of this trained model may include, for each CBCT projection, to use the model to infer nonlinearity-free projections and then reconstruct a 3D CBCT image with these new projections. As above, this use case may further include creation of a 4D CBCT image volume from multiple reconstructed 3D CBCT images.

In a third specific aspect the model (e.g., neural network) is trained based on a single patient-specific patient dataset, such as a planning CT, to infer large field-of-view (FOV) projections from limited FOV projections. The use case of this trained model may include, for each CBCT projection, to use the model to infer large FOV projections and reconstruct a 3D CBCT image (and, in some examples, a 4D CBCT image volume) with these projections.

Figure 11:
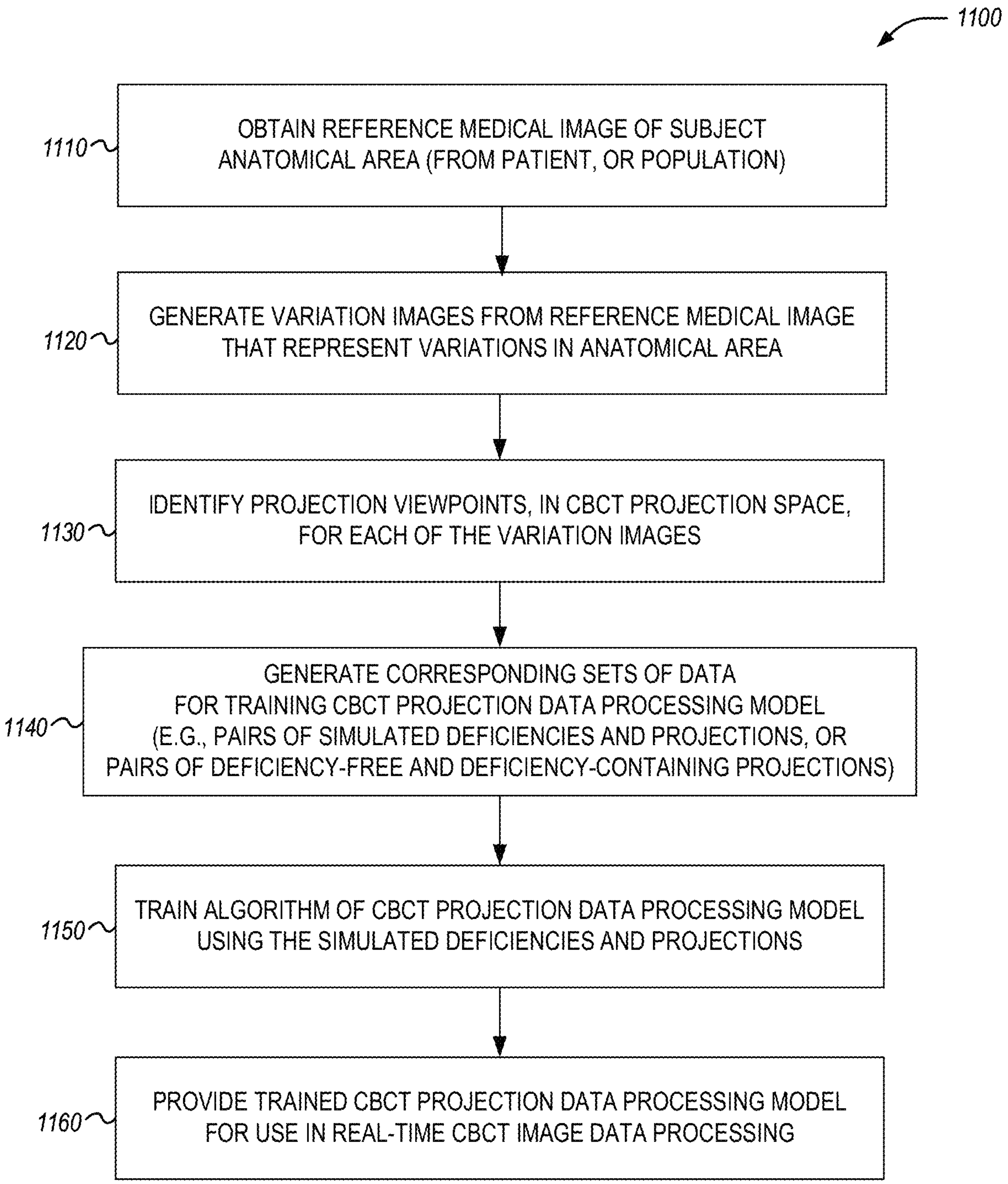
FIG. 11 illustrates a flowchart of a method of training an image processing model for artifact removal in real-time CBCT image processing, according to some examples.

FIG. 11 illustrates a flowchart of an example method of training a data processing model for real-time CBCT image data processing. For instance, the following features of flowchart 1100 may be integrated or adapted with the training discussed with reference to model training in FIGS. 3, 4, 6, and 7A to 7C.

At operation 1110: a reference medical image (or medical images, or imaging volume from which such images can be extracted) of a subject anatomical area is obtained, from a patient or a population of patients. For instance, a plurality of reference medical images may be obtained from one or more prior CT scans or one or more prior CBCT scans of the patient. Or, a plurality of reference medical images may be obtained from each of a plurality of human subjects for training from the population of patients.

At operation 1120: variation images, which provide variation of the representations of the anatomical area, are generated from the reference medical image. Such variation may include geometrical augmentations (e.g., rotation) or changes (e.g., deformation) to the representations of the anatomical area.

At operation 1130: projection viewpoints are identified, in a CBCT projection space, for each of the variation images. Such viewpoints may correspond to the projection angles used for capturing CBCT projections, or additional angles.

At operation 1140: corresponding sets (e.g., pairs) of projections and simulated aspects (e.g., simulated deficiencies) are generated, at each of the projection viewpoints. Such simulated aspects may be added into a new set of projections. For instance, this may result in producing pairs of generated CBCT projections that include simulated deficiencies and generated CBCT projections that do not include the simulated deficiencies.

At operation 1150: an algorithm of a data processing model (e.g., a convolutional neural network) is trained using the corresponding sets of the CBCT projections and the simulated aspects of the CBCT projections. In an example, the training is performed with pairs of generated CBCT projections that include the simulated aspects (e.g., projections that include deficiencies such as scatter or simulated artifacts) and generated CBCT projections that do not include the simulated aspects (e.g., clean projections that do not include deficiencies such as scatter or simulated artifacts).

At operation 1160: the trained model is provided for use in real-time CBCT data processing, including in connection with radiotherapy settings. However, in other examples, other post-processing or radiology image processing use cases (including use cases not involving radiotherapy) may use the trained model.

Figure 12:
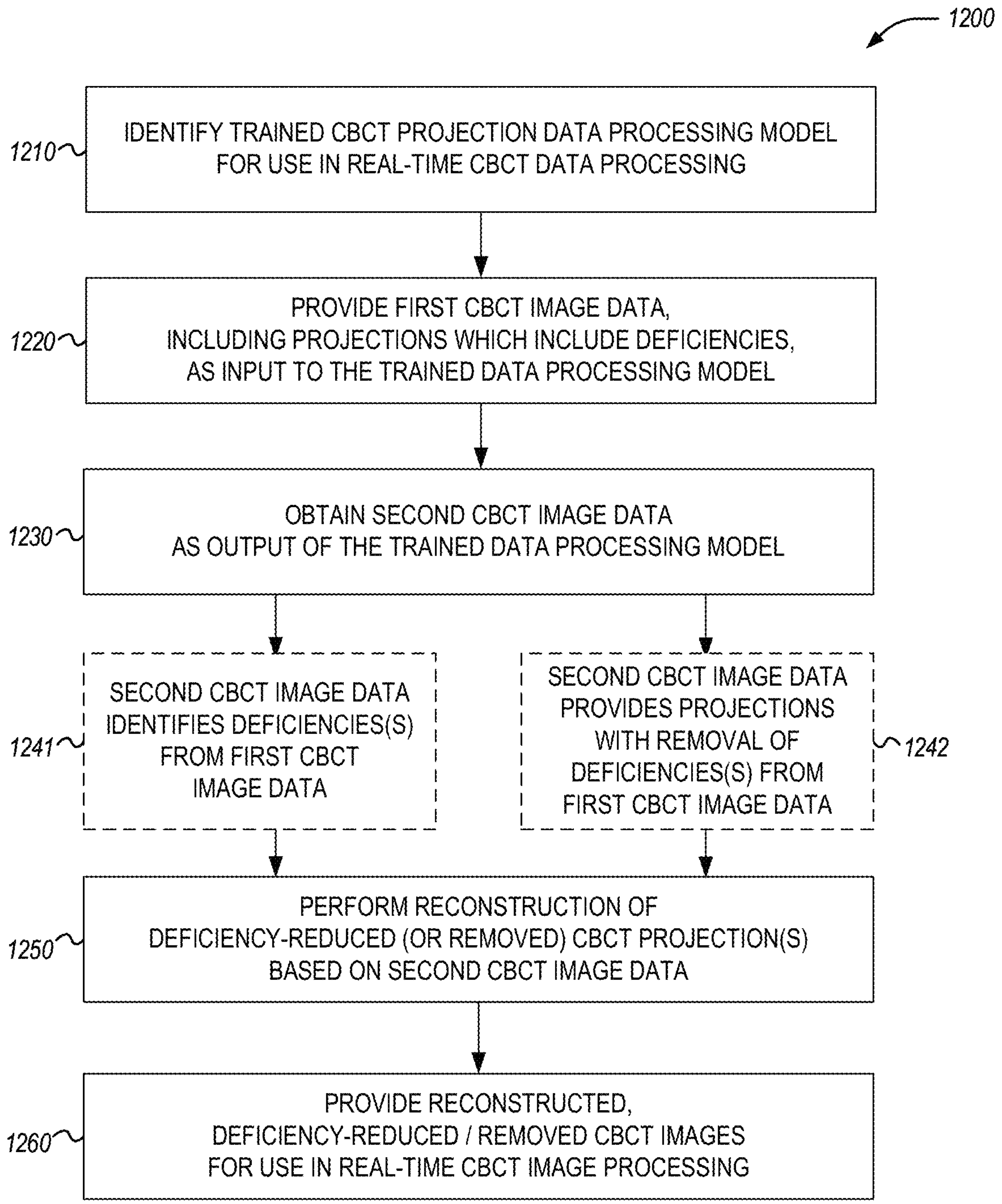
FIG. 12 illustrates a flowchart of a method of using a trained image processing model for artifact removal for use in real-time CBCT image processing, according to some examples.

FIG. 12 illustrates a flowchart of a method of using a trained data processing model for use in real-time CBCT data processing, according to some examples. The trained data processing model may be integrated or adapted with the model training discussed above with reference to FIGS. 3, 4, 6, 7A to 7C, and 11.

At operation 1210: the trained image processing model (e.g., a model trained as discussed above with reference to FIG. 11) is identified for use in real-time CBCT data processing. This model may be trained from patient-specific or population-based reference images, as discussed above.

At operation 1220: a first set of CBCT image data, that includes projections which include deficiencies (e.g., artifacts or incomplete/missing information), is provided as input to the trained image processing model.

At operation 1230: a second set of CBCT image data is generated as output of the trained image processing model. In a first example, at operation 1241, the second CBCT image data provides an estimation (prediction) of deficiencies (e.g., artifact(s)) in the projections of the first CBCT image data. In a second example, at operation 1242, the second CBCT image data provides projections that have a removal or reduction of the deficiencies (e.g., removal of artifact(s), or additional information that corrects the deficiencies) in the projections of the first CBCT image data.

At operation 1250: reconstruction of one or more CBCT image(s) are performed on deficiency-reduced (or deficiency-removed) CBCT projections, based on the second CBCT image data.

At operation 1260: the reconstructed deficiency-reduced CBCT image(s) are provided for use in real-time CBCT image processing, such as in adaptive radiotherapy workflows based on CBCT imaging.

FIG. 13 illustrates a flowchart of a method performed by a computing system for image processing and artifact removal within radiotherapy workflows, according to some examples. FIG. 13 is a flowchart 1300 illustrating example operations for performing training and treatment workflows (including those depicted among FIGS. 3-6, 7A-7C, and 8-12), according to various examples. These operations may be implemented at processing hardware of the image processing computing system 110, for instance, and may integrate aspects of the training and inference workflows depicted among FIGS. 3-6, 7A-7C, and 8-12.

At operation 1310, CBCT image data is captured, on an ongoing basis, to obtain real-time imaging data from patient.

At operation 1320, the trained regression model (e.g., trained as in FIG. 11, discussed above) is used to identify estimated (predicted) deficiencies in projections of CBCT image data (e.g., using the inference workflow as in FIG. 11, discussed above).

At operation 1330, the estimated (predicted) deficiencies in the CBCT projections are removed, using a data processing workflow (e.g., which identifies or subtracts the identified deficiencies) or directly from output of the model itself (e.g., using a trained model which outputs one or more corrected CBCT projections). At operation 1340, CBCT image reconstruction is performed on the deficiency removed/deficiency-reduced CBCT projections.

At operation 1350, a state of a patient (e.g., a patient for radiotherapy treatment) is identified, based on the reconstructed CBCT image(s). As a first example, at operation 1360, a radiation therapy target is located within a patient in real-time using the identified state. As a second example, at operation 1370, a radiation therapy dosage is tracked within the patient in real-time using the identified state.

At operation 1380, image processing computing system 110 directs or controls radiation therapy, using a treatment machine, to a radiation therapy target according to the identified patient state. It will be understood that a variety of existing approaches for modifying or adapting radiotherapy treatment may occur based on the controlled therapy or identified patient state, once correctly estimated.

The processes depicted in flowcharts 1100, 1200, 1300 with FIGS. 11 to 13 may be embodied in computer-readable instructions for execution by one or more processors such that the operations of the process may be performed, for instance, in part or in whole by the functional components of the image processing computing system 110. However, in other examples, at least some of the operations of the process may be deployed on various other hardware configurations. Some or all of the operations of process can be in parallel, out of order, or entirely omitted.

FIG. 14 illustrates a block diagram of an example of a machine 1400 on which one or more of the methods as discussed herein can be implemented. In one or more examples, one or more items of the image processing computing system 110 can be implemented by the machine 1400. In alternative examples, the machine 1400 operates as a standalone device or may be connected (e.g., networked) to other machines. In one or more examples, the image processing computing system 110 can include one or more of the items of the machine 1400. In a networked deployment, the machine 1400 may operate in the capacity of a server or a client machine in server-client network environment, or as a peer machine in a peer-to-peer (or distributed) network environment. The machine may be a personal computer (PC), server, a tablet, smartphone, a web appliance, edge computing device, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1400 includes processing circuitry or processor 1402 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 1421 (e.g., a transducer that converts one form of energy (e.g., light, heat, electrical, mechanical, or other energy) to another form of energy), or the like, or a combination thereof), a main memory 1404 and a static memory 1406, which communicate with each other via a bus 1408. The machine 1400 (e.g., computer system) may further include a video display device 1410 (e.g., a liquid crystal display (LCD) or a cathode ray tube (CRT)). The machine 1400 also includes an alphanumeric input device 1412 (e.g., a keyboard), a user interface (UI) navigation device 1414 (e.g., a mouse), a disk drive or mass storage unit 1416, a signal generation device 1418 (e.g., a speaker), and a network interface device 1420.

The disk drive unit 1416 includes a machine-readable medium 1422 on which is stored one or more sets of instructions and data structures (e.g., software) 1424 embodying or utilized by any one or more of the methodologies or functions described herein. The instructions 1424 may also reside, completely or at least partially, within the main memory 1404 and/or within the processor 1402 during execution thereof by the machine 1400, the main memory 1404 and the processor 1402 also constituting machine-readable media.

The machine 1400 as illustrated includes an output controller 1428. The output controller 1428 manages data flow to/from the machine 1400. The output controller 1428 is sometimes called a device controller, with software that directly interacts with the output controller 1428 being called a device driver.

While the machine-readable medium 1422 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1424 may further be transmitted or received over a communications network 1426 using a transmission medium. The instructions 1424 may be transmitted using the network interface device 1420 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and 4G/5G data networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

ADDITIONAL NOTES

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In an embodiment, the computer-readable storage medium may have encoded a data structure for treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, C#, Java, Python, CUDA programming, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A computer-implemented method for training a regression model for cone-beam computed tomography (CBCT) data processing, the method comprising:

obtaining a reference medical image of an anatomical area;

generating, from the reference medical image, a plurality of variation images, wherein the plurality of variation images provide variation in representations of the anatomical area;

identifying projection viewpoints, in a CBCT projection space, for each of the plurality of variation images;

generating, at each of the projection viewpoints, a set of CBCT projections and a corresponding set of simulated aspects of the CBCT projections; and training the regression model, using the corresponding sets of the CBCT projections and the simulated aspects of the CBCT projections generated from each of the projection viewpoints;

wherein training the regression model includes training at each respective projection viewpoint with pairs of generated CBCT projections that include simulated deficiencies and generated CBCT projections that do not include the simulated deficiencies; and wherein the trained regression model is configured to receive a newly captured CBCT projection that includes one or more deficiencies as input, and wherein the trained regression model is configured to provide a corrected CBCT projection as output.

2. The method of claim 1, wherein the trained regression model is adapted to correct one or more deficiencies in the newly captured CBCT projection caused by scatter, and wherein the pairs of generated CBCT projections for training comprise CBCT projections that include simulated scatter and CBCT projections that do not include the simulated scatter.

3. The method of claim 1, wherein the trained regression model is adapted to correct one or more deficiencies in the newly captured CBCT projection caused by a foreign material, and wherein the pairs of generated CBCT projections for training comprise CBCT projections that include simulated artifacts caused by the foreign material and CBCT projections that remove the simulated artifacts caused by the foreign material.

4. The method of claim 3, wherein the foreign material is metal, and wherein the CBCT projections that remove the simulated artifacts are produced using at least one metal artifact reduction algorithm.

5. The method of claim 1, wherein the trained regression model is adapted to correct one or more deficiencies in the newly captured CBCT projection caused by beam divergence, and wherein the corrected CBCT projection is computed in parallel-beam geometry.

6. The method of claim 1, wherein the plurality of variation images comprise a first plurality of CBCT projections generated with a first field of view, and wherein the trained regression model is configured to receive as input a second plurality of CBCT projections having a second field of view that differs from the first field of view.

7. The method of claim 1, wherein the plurality of variation images are generated by geometrical augmentations or changes to the representations of the anatomical area, and wherein the projection viewpoints correspond to a plurality of projection angles for capturing CBCT projections.

8. The method of claim 1, wherein the reference medical image is a 3D image provided from a computed tomography (CT) scan, and wherein the method further includes training of the regression model using a plurality of reference medical images from the CT scan.

9. The method of claim 1, wherein the reference medical image is from a human patient, and wherein the trained regression model is used for radiotherapy treatment of the human patient.

10. The method of claim 9, wherein the method further includes training of the regression model using a plurality of reference medical images from one or more prior computed tomography (CT) scans or one or more prior CBCT scans of the human patient.

11. The method of claim 1, wherein the reference medical image is provided from one of a plurality of human subjects, and wherein the method further includes training of the model using a plurality of reference medical images from each of the plurality of human subjects.

12. A computer-implemented method for using a trained regression model for cone-beam computed tomography (CBCT) data processing, the method comprising:

accessing a trained regression model configured for removing deficiencies in CBCT projections, wherein the trained regression model is trained using corresponding sets of simulated deficiencies and CBCT projections at each of a plurality of projection viewpoints in a CBCT projection space, wherein training of the trained regression model includes training at each respective projection viewpoint with pairs of generated CBCT projections that include the simulated deficiencies and generated CBCT projection images that do not include the simulated deficiencies, and wherein the sets of simulated deficiencies and CBCT projections are generated based on a reference medical image;

providing a first plurality of CBCT projections as an input to the trained regression model, wherein the first plurality of CBCT projections include one or more deficiencies; and obtaining a second plurality of CBCT projections as an output of the trained regression model, wherein the second plurality of CBCT projections include corrections to the one or more deficiencies.

13. The method of claim 12, wherein the one or more deficiencies in the first plurality of CBCT projections are caused by scatter, and wherein the pairs of generated CBCT projections used for training comprise CBCT projections that include simulated scatter and CBCT projections that do not include the simulated scatter.

14. The method of claim 12, wherein the one or more deficiencies in the first plurality of CBCT projections are caused by a foreign material, and wherein the pairs of generated CBCT projections used for training include CBCT projections that include simulated artifacts caused by the foreign material and CBCT projections that remove the simulated artifacts caused by the foreign material.

15. The method of claim 14, wherein the foreign material is metal, and wherein the CBCT projections that remove the simulated artifacts are produced using at least one metal artifact reduction algorithm.

16. The method of claim 12, wherein the deficiencies in the first plurality of CBCT projections are caused by beam divergence, and wherein the second plurality of CBCT projections are produced based on parallel-beam geometry.

17. The method of claim 12, wherein the first plurality of CBCT projections are captured with a first field of view, and wherein the CBCT projections used for training are generated with a second field of view that differs from the first field of view.

18. The method of claim 12, wherein the reference medical image used for training is one of a plurality of 3D images provided from a computed tomography (CT) scan.

19. The method of claim 12, further comprising:

performing reconstruction of a 3D CBCT image from the second plurality of CBCT projections.

20. The method of claim 19, wherein the reference medical image used for training is from a human patient, and wherein the 3D CBCT image is used for radiotherapy treatment of the human patient.

21. The method of claim 12, wherein the trained regression model is trained based on reference images captured from a plurality of human subjects.

22. A non-transitory computer-readable storage medium comprising computer-readable instructions for training a regression model to process cone-beam computed tomography (CBCT) data, wherein the instructions, when executed, cause a computing machine to perform operations comprising:

obtaining a reference medical image of an anatomical area;

generating, from the reference medical image, a plurality of variation images, wherein the plurality of variation images provide variation in representations of the anatomical area;

identifying projection viewpoints, in a CBCT projection space, for each of the plurality of variation images;

generating, at each of the projection viewpoints, a set of CBCT projections and a corresponding set of simulated aspects of the CBCT projections; and training the regression model, using the corresponding sets of the CBCT projections and the simulated aspects of the CBCT projections generated from each of the projection viewpoints;

wherein training the regression model includes training at each respective projection viewpoint with pairs of generated CBCT projections that include simulated deficiencies and generated CBCT projections that do not include the simulated deficiencies; and wherein the trained regression model is configured to receive a newly captured CBCT projection that includes one or more deficiencies as input, and wherein the trained regression model is configured to provide a corrected CBCT projection as output.

23. A non-transitory computer-readable storage medium comprising computer-readable instructions for using a trained regression model to process cone-beam computed tomography (CBCT) data, wherein the instructions, when executed, cause a computing machine to perform operations comprising:

accessing a trained regression model configured for removing deficiencies in CBCT projections, wherein the trained regression model is trained using corresponding sets of simulated deficiencies and CBCT projections at each of a plurality of projection viewpoints in a CBCT projection space, wherein training of the trained regression model includes training at each respective projection viewpoint with pairs of generated CBCT projections that include the simulated deficiencies and generated CBCT projection images that do not include the simulated deficiencies, and wherein the sets of simulated deficiencies and CBCT projections are generated based on a reference medical image;

providing a first plurality of CBCT projections as an input to the trained regression model, wherein the first plurality of CBCT projections include one or more deficiencies; and obtaining a second plurality of CBCT projections as an output of the trained regression model, wherein the second plurality of CBCT projections include corrections to the one or more deficiencies.

* * * * *